United States Patent
Johansen et al.

(12)

(10) Patent No.: US 6,441,152 B1
(45) Date of Patent: Aug. 27, 2002

(54) METHODS, KITS AND COMPOSITIONS FOR THE IDENTIFICATION OF NUCLEIC ACIDS ELECTROSTATICALLY BOUND TO MATRICES

(75) Inventors: Jack T. Johansen, Concord; Jens J. Hyldig-Nielsen, Holliston; Mark J. Fiandaca, Princeton; James M. Coull, Westford, all of MA (US)

(73) Assignee: Boston Probes, Inc., Bedford, MA (US)

( * ) Notice: Subject to any disclaimer, the term of this patent is extended or adjusted under 35 U.S.C. 154(b) by 0 days.

(21) Appl. No.: 09/456,773

(22) Filed: Dec. 8, 1999

Related U.S. Application Data

(60) Provisional application No. 60/111,439, filed on Dec. 8, 1998.

(51) Int. Cl.[7] .................. C07H 21/02; C07H 21/04; C07H 21/00; C12Q 1/68; C12P 19/34
(52) U.S. Cl. ................ 536/23.1; 536/24.3; 536/24.33; 536/25.3; 536/25.32; 435/6; 435/91.1
(58) Field of Search ................ 435/6, 91.1, 91.2; 436/94; 536/23.1, 24.3, 24.33, 25.3, 25.32

(56) References Cited

U.S. PATENT DOCUMENTS

| | | | |
|---|---|---|---|
| 4,943,522 A | 7/1990 | Eisinger ..................... 435/7 |
| 4,956,302 A | 9/1990 | Gordon ..................... 436/161 |
| 4,997,932 A | * 3/1991 | Reardon et al. ............. 536/27 |
| 5,200,314 A | 4/1993 | Urdea ......................... 435/6 |
| 5,234,809 A | 8/1993 | Boom ......................... 435/91 |
| 5,405,951 A | 4/1995 | Woodard ................. 536/25.41 |
| 5,415,994 A | 5/1995 | Imrich ......................... 435/5 |
| 5,438,127 A | 8/1995 | Woodard ................... 536/25.4 |
| 5,438,129 A | 8/1995 | Woodard ................... 536/25.4 |
| 5,527,675 A | 6/1996 | Coull .......................... 435/6 |
| 5,539,082 A | 7/1996 | Nielsen ..................... 530/300 |
| 5,599,667 A | 2/1997 | Arnold ......................... 435/6 |
| 5,612,458 A | * 3/1997 | Hyldig-Nielsen et al. ................. 530/388.21 |
| 5,623,049 A | 4/1997 | Lobberding ............... 530/300 |
| 5,710,005 A | 1/1998 | Rittenburg ................... 435/6 |
| 5,714,331 A | 2/1998 | Buchardt ..................... 435/6 |
| 5,736,336 A | 4/1998 | Buchardt ..................... 435/6 |
| 5,741,647 A | 4/1998 | Tam ............................ 435/6 |
| 5,747,349 A | 5/1998 | Van den Engh ........... 436/172 |
| 5,750,338 A | 5/1998 | Collins ........................ 435/6 |
| 5,770,460 A | 6/1998 | Pawlak ..................... 436/510 |
| 5,773,571 A | 6/1998 | Nielsen ..................... 530/300 |
| 5,780,233 A | 7/1998 | Guo ............................ 435/6 |
| 5,786,461 A | 7/1998 | Buchardt .................. 536/18.7 |
| 5,798,273 A | 8/1998 | Shuler ..................... 436/514 |
| 5,807,522 A | * 9/1998 | Brown et al. ............... 422/50 |
| 5,834,181 A | 11/1998 | Shuber ......................... 435/5 |

(List continued on next page.)

FOREIGN PATENT DOCUMENTS

| | | |
|---|---|---|
| EP | 0221308 A | 5/1987 |
| EP | 0411186 A | 2/1991 |
| WO | WO94/25477 | 11/1994 |
| WO | WO95/15974 | 6/1995 |
| WO | WO95/17430 | 6/1995 |
| WO | WO96/04000 | 2/1996 |
| WO | WO97/12995 | 4/1997 |
| WO | WO97/29825 | * 8/1997 |
| WO | WO97/45539 | 12/1997 |
| WO | WO98/20019 | 5/1998 |
| WO | WO98/38334 | 9/1998 |
| WO | WO98/46797 | 10/1998 |
| WO | WO99/21881 | 5/1999 |
| WO | WO 99/21881 | * 5/1999 |
| WO | WO99/22018 | 5/1999 |
| WO | WO99/55916 | 11/1999 |

OTHER PUBLICATIONS

Ortiz et al., PNA molecular beacons for rapid detection of PCR amplicons. Mole. Cell. Probes 12, 219–226, Aug. 1998.*

Boffa et al., Isolation of active genes containing CAG repeats by DNA strand invasion by a peptide nucleic acid. 92, 1901–1905, 1995.*

Tomac et al., Ionic effects on the stability and conformation of peptide nucleic acid complexes. 118, 5544–5552, 1996.*

(List continued on next page.)

Primary Examiner—Ethan C. Whisenant
Assistant Examiner—Frank Lu
(74) Attorney, Agent, or Firm—Brian D. Gildea

(57) ABSTRACT

This invention pertains to methods, kits and compositions suitable for the detection, identification and/or quantitation of nucleic acids which are electrostatically immobilized to matrices using non-nucleotide probes which sequence specifically hybridize to one or more target sequences of the nucleic acid but do not otherwise substantially interact with the matrix. Once the nucleic acid is immobilized, the detectable non-nucleotide probe/target sequence complex, formed before or after the immobilization of the nucleic acid, can be detected, identified or quantitated under a wide range of assay conditions as a means to detect, identify or quantitate the target sequence in the sample. Because it is reversibly bound, the non-nucleotide probe/target sequence can optionally be removed from the matrix for detecting, identifying or quantitating the target sequence in the sample. Because the non-nucleotide probe/target sequence is protected against degradation, it is another advantage of this invention that the sample can be treated with enzymes which degrade sample components, either before or after the nucleic acid is bound to the matrix, in order to "clean up" the sample (e.g. a complex biological sample such as a cell lysate) and thereby improve the detection, identification or quantitation of the target sequence in the sample. The methods, kits and compositions of this invention are therefore particularly well suited for the analysis, and particularly single point mutation analysis, in a particle assay, in an array assay, in a nuclease digestion/protection assay and/or in a line assay format. When utilized in combination with non-nucleotide "Beacon" probes, the invention is particularly well suited for use in a self-indicating assay format.

44 Claims, 6 Drawing Sheets

U.S. PATENT DOCUMENTS

| | | | | |
|---|---|---|---|---|
| 5,849,486 | A | | 12/1998 | Heller ........................... 435/6 |
| 5,861,250 | A | * | 1/1999 | Stanley et al. ................. 435/6 |
| 5,888,733 | A | | 3/1999 | Hyldig-Nielsen .............. 435/6 |
| 5,916,521 | A | | 6/1999 | Bunce ......................... 422/56 |
| 5,925,517 | A | * | 7/1999 | Tyagi et al. ................... 435/6 |
| 5,932,711 | A | | 8/1999 | Boles et al. ............... 536/22.1 |
| 5,985,563 | A | | 11/1999 | Hyldig-Nielsen .............. 435/6 |
| 5,985,930 | A | * | 11/1999 | Pasinetti et al. ............ 514/607 |
| 6,020,126 | A | | 2/2000 | Carlsson et al. ............... 435/6 |
| 6,110,676 | A | | 8/2000 | Coull et al. | |
| 6,225,052 | B1 | * | 5/2001 | Batz et al. ..................... 435/6 |

OTHER PUBLICATIONS

Weiler et al., Hybridization based DNA screening on peptide nucleic acid (PNA) oligomer arrays. Nucleic Acids Res. 25, 2792–2799, 1997.*
Stratagene Catalog (1988), p. 39, Published by Stratagene, 11011 North Torrey Pines Road, La Jolla, CA 92037.*
Edelstein, Evaluation of the Gen–Probe DNA probe for the detection of Legionallae in culture. J. Clin. Microbiology, 23, 481–484, 1986.*
Levison et al., Recent developments of magnetic beads for use in nucleic acid purification. J. Chromatography A, 816, 107–111, 1998.*
Amersham Pharmacia Biotech Catalog, Bio Directory: Ion Exchange. Amersham Pharmacia Biotech, Inc. 12 520–531 (1999).
Corey, D.R., Peptide nucleic acids: expanding the scope of nucleic acid recognition. Tibtech. 15, 224–229, (1997).
Lehninger, A.L., Vitamins and Trace Elements In the Function of Enzymes; Biomolecules. Principals of Biochemistry. 10, 259–260, (1982).
Miller, F. Jr., et al, Electric Forces—Charges At Rest. Concepts in Physics. 14, 234–247 (1974).
Nielsen, P.E., et al, Peptide Nucleic Acid (PNA): A DNA Mimic with a Peptide Backbone. Bioconjugate Chemistry. 5, 3–7, (1994).
Pierce Catalog and Handbook, Avidin—Biotin. Pierce. T123–T200, Electrophoresis. Pierce. T201–T207, Immunoassays. Pierce. T289–T334. (1994).
Stryer, L., DNA: Genetic Role, Structure, and Replication. Biochemistry. 24, 559–596, (1981).
Edman, C.F. et al, Electric field directed nucleic acid hybridization on microchips. Nucl. Acids. Res. 25, 4907–4914 (1997).
Arya, D.P. et al, Positively charged deoxynucleic methylthioureas: synthesis and binding properties of pentameeric thymidly methylthiourea. J. Am. Chem. Soc. 120, 12419–12427 (1998).
Cantin, M. et al, Synthesis of the monomeric building blocks of Z–olefinic PNA (ZOPA) containing the bases adenine and thymine. Tett. Lett. 38, 4211–4214 (1997).
Ciapetti, P. et al, Synthesis of N–Fmoc–α–amino acids carrying the four DNA nucleobases in the side chain. Tetrahedron 53, 1167–1176 (1997).
Diederichen, U., Alanyl–PNA homoduplex: A–T pairing with the N7–regioisomer of adenine. Bioorg. & Med. Chem. Lett. 8, 165–168 (1998).
Diederichsen, U. et al, Self–pairing PNA with alternating alanyl/homoalanyl backbone. Tett. Lett. 37, 475–478 (1996).

Egholm, M. et al, PNA hybridizes to complementary oligonucleotides obeying the Watson–Crick hydrogen–bonding rules. Nature 365, 566–568 (1993).
Fuji, M. et al, Nucleic acid analog peptide (NAAP)2, syntheses and properties of novel DNA analog peptides containing nucleobase linked β–aminoalanine. Bioorg. & Med. Chem. Lett, 7, 637–640 (1997).
Gildea, B.D. et al, PNA solubility enhancers. Tett. Lett. 39, 7255–7258 (1998).
Guo, Z. et al, Enhanced discrimination of single nucleotide polymorphisms by artificial mismatch hybridization. Nature Biotech. 15, 331–335 (1997).
Jordan, S. et al, New hetero–oligomeric peptide nucleic acids with improved binding properties to complementary DNA. Bioorg. & Med. Chem. Lett. 7, 687–690 (1997).
Kohne, D.E. et al, Hydroxyapatite techniques for nucleic acid reassociation. Procedures in Nucleic Acids Research vol. 2, Edited by G.L. Cantoni and David R. Davies, 500–512.
Krotz, A.H. et al, Synthesis of 'retro–inverso' peptide nucleic acids: 2. oligomerization and stability. Tett. Lett. 36, 6941–6944 (1995).
Lagriffoul, P–H. et al, The synthesis, co–oligomerization and hybridization of a thymine—thymine heterodimer containing PNA. Bioorg. & Med. Chem. Lett. 4, 1081–1082 (1994).
Lagriffoule, P. et al, Peptide nucleic acids with a conformationally constrained chiral cyclohexyl–derived backbone. Chem. Eur. J. 3, 912–919 (1997).
Lowe, G. et al, Dipeptides bearing nucleobases for the synthesis of novel peptide nucleic acids. J. Chem. Soc., Perkin Trans. 1, 547–554.
Lowe, G. et al, Solid–phase of novel peptide nucleic acids. J. Chem. Soc., Perkin Trans. 1, 555–560 (1997).
Lowe, G. et al, Amino acids bearing nucleobases for the synthesis of novel peptide nucleic acids. J. Chem. Soc, Perkin Trans. 1, 539–546 (1997).
Nielsen, P.E. et al, Peptide nucleic acids (PNAs): Potential anti–sense and anti–gene agents. Anti–Cancer Drug Design 8, 53–63 (1993).
Petersen, K.H. et al, Synthesis and oligomerization of Nδ–Boc–Nα–(thymin–1–ylacetyl)orthinine. Bioorg. & Med. Chem. Lett. 6, 793–796 (1996).
Pluskal, M. et al, Peptide nucleic acid probes and their application in DNA and RNA blot hybridization analysis. Abstract #35, American Society for Biochem. And Mol. Biol. 85$^{th}$ Annual Meeting, 1994.
Su, X. et al, Cellulose as a matrix for nucleic acid purification. Analy. Biochem. 267, 415–418 (1999).
Tomac, S. et al, Ionic effects on the stability and conformation of peptide nucleic acid complexes. J. Am. Chem. Soc. 118, 5544–5552 (1996).
Weiler, J. et al, Hybridisation based on DNA screening on peptide nucleic acid (PNA) oligomer arrays. Nucl. Acids Res. 25, 2792–2799 (1997).
Yaron, A. et al, Intramolecularly quenched fluorogenic substrates for hydrolytic enzymes. Anal. Biochem. 95, 228–235 (1979).

* cited by examiner

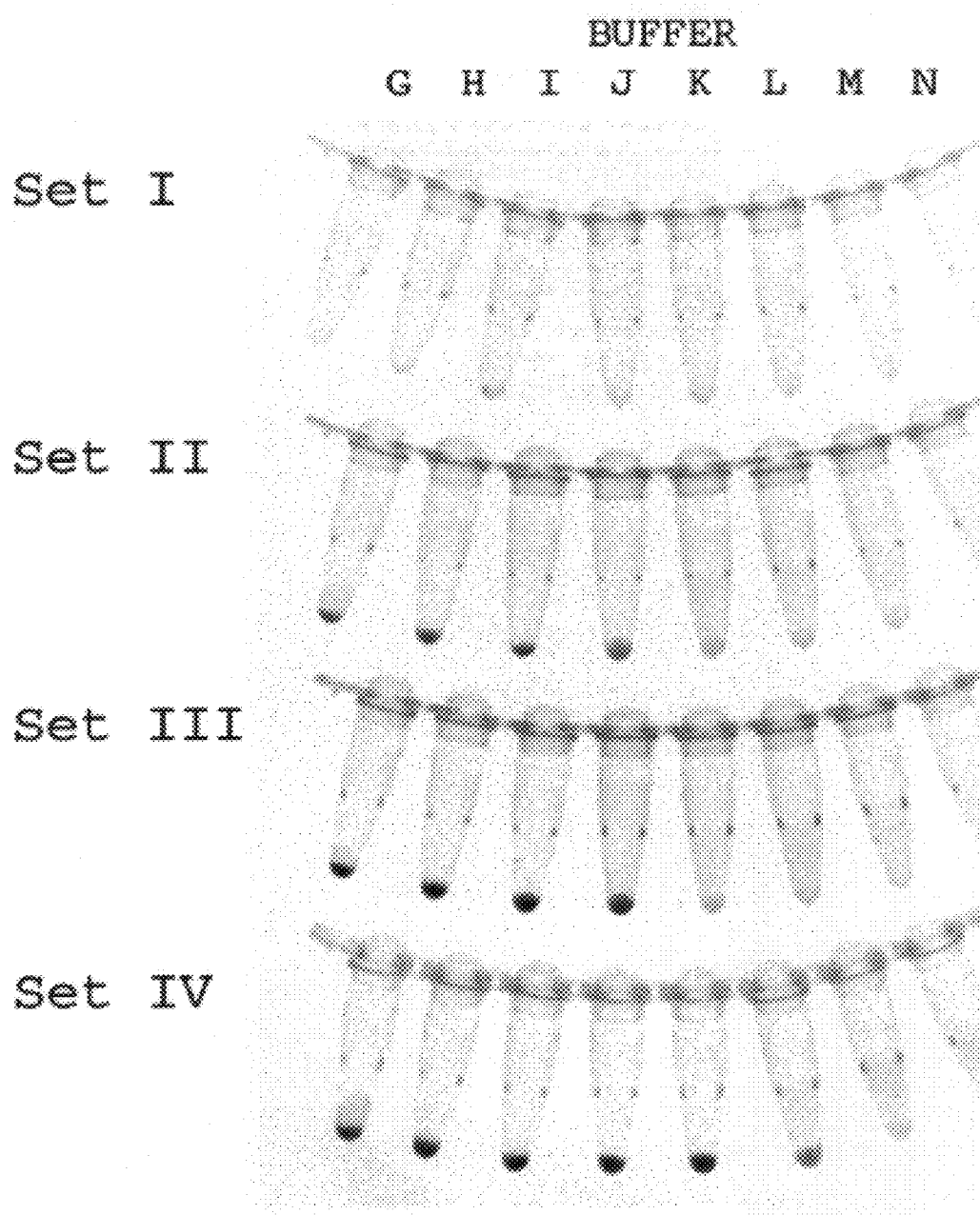

A　　　　　B　　　　　C

A　　　　　B　　　　　C

METHODS, KITS AND COMPOSITIONS FOR THE IDENTIFICATION OF NUCLEIC ACIDS ELECTROSTATICALLY BOUND TO MATRICES

CROSS REFERENCE TO RELATED APPLICATIONS

This application claims the benefit of U.S. Provisional Patent Application Serial No. 60/111,439 filed on Dec. 8, 1998.

BACKGROUND OF THE INVENTION

1. Field of the Invention

This invention is related to the field of probe-based detection, analysis and quantitation of nucleic acids which are electrostatically immobilized to matrices. The methods, kits and compositions of this invention are particularly well suited for the analysis, and particularly single point mutation analysis, in a particle assay, in an array assay, in a nuclease digestion/protection assay, in a line assay and/or in a self-indicating assay format.

2. Description of the Related Art

Nucleic acid hybridization is a fundamental process in molecular biology. Probe-based assays are useful in the detection, quantitation and analysis of nucleic acids. Nucleic acid probes have long been used to analyze samples for the presence of nucleic acid from bacteria, eucarya, fungi, virus or other organisms and are also useful in examining genetically-based disease states or clinical conditions of interest in single cells as well as in tissues.

Sample prep methods which describe the repetitive capture and release of target sequences to and from supports (e.g. magnetic beads) as a means to remove non-target polynucleotides, debris and impurities which tend to introduce background in a hybridization assay are known in the art (See: Collins et al., U.S. Pat. No. 5,750,338). Generally, the sample prep methods of Collins et al. can be used in most embodiments of traditional hybridization assays provided however that the target nucleic acid is first immobilized to a support and thereafter released from the support such that, when released, it is substantially free of sample impurities, debris, and extraneous polynucleotides. The Collins et al. invention, however, requires that the probe or probes must be associated with or capable of associating with the support under binding conditions to thereby immobilize the nucleic acid of interest to the support (See: Collins et al. at col. 4, line 55 to col. 5, line 13).

A probe based sample prep method for removing contaminants prior to PCR reaction has been described by Goldin et al. (See: U.S. Pat. No. 5,200,314). This process requires an analyte-capture probe having both an analyte binding region and a first specific binding partner. Like the Collins et al. invention, the Goldin et al. invention requires that the analyte-capture probe interact with the support as the specific means through which the target sequence becomes immobilized.

Polycationic solid supports have been used for the analysis and purification of nucleic acids, including the purification of polynucleotides from solutions containing contaminants See: Arnold et al.; U.S. Pat. No. 5,599,667). Arnold et al. describe assays which use solid supports as a means to separate polynucleotides, and hybrids thereof formed with a nucleotide probe, from unhybridized probe (See: Abstract to U.S. Pat. No. 5,599,667). The invention is premised upon ". . . the discovery that polycationic solid supports can be used to selectively adsorb nucleotide multimers according to their size (emphasis added), larger multimers being more tightly bound to the support than smaller ones." (See: Col. 4, lines 39–44). The methods can also be used to separate the nucleotide multimers from non-nucleotidic material (See: Col. 5, lines 25–28).

A substantial limitation of the Arnold et al. invention is the interplay which exists between the composition of the cationic solid support and the formulation of contacting solutions as well as the interplay between two or more of the contacting solutions (See: Col. 7, line 24 to Col. 8, line 32) which are required to discriminate between nucleotide multimers (See: Col. 8, lines 39–41). An example of a laborious protocol for arriving at a proper cation density for a solid support can be found at col. 9, lines 36–52 and the method for determining the buffer concentration suitable for separating polynucleotides and nucleotide probes can be found at col. 9, lines 53–63. Similarly, the separation solution must be carefully designed (See: Col. 10. lines 9–12), presumably using the laborious method of trial and error as described for determining the cation density of the solid support. This requirement for substantial optimization of assay conditions within a very narrow operating range results because electrostatic immobilization of nucleic acid is a relatively non-specific process and therefore it is difficult to electrostatically immobilize a negatively charged target nucleic acid to a cationic surface without the positively charged matrix also exhibiting a strong affinity for the negatively charged nucleic acid probe. Since the separation of nucleotide multimers (nucleotide probe/target hybrids from excess nucleotide probe) occurs within a narrow range of conditions, which may not necessarily be optimal for the discrimination of hybridization, the hybrids still immobilized according to the Arnold et al. invention may not be truly indicative of the presence of a target sequence. Consequently, the applicability of the assays of Arnold et al. are of limited practical utility.

An invention related to achieving nucleic acid has recently been described (See: Gerdes et al.; WO98/46797). Gerdes et al. use highly electropositive solid phase materials to capture nucleic acids (See. p. 5, line 24 to p. 6, line 14) for repetitive analyses. However, a substantial limitation of the Gerdes et al. invention is that the nucleic acid must be irreversibly bound to the highly electropositive solid phase material.

Methods for the high throughput screening for sequences or genetic alterations in nucleic acid have been described (See: Shuber, A. P.; U.S. Pat. No. 5,834,181). Shuber describes the analysis of arrays of immobilized nucleic acids, and suggests immobilization of the nucleic acid to nitocellulose or a charged nylon membrane (See: col. 6, lines 41–64). Suggested purine and pyrimidine containing polymers which may be used for analyzing immobilized nucleic acid include peptide nucleic acid (See: col. 5, lines 15–20), but the polymers must necessarily be tagged or labeled since the detection methods rely on a tag or label being incorporated into the polymer (See: col. 8, line 58 to col. 9, line 3). The assays of Shuber require a perfect complement between probe and target sequence (See: col. 8, lines 52–57). In order to achieve proper discrimination, a laborious empirical process of trial and error is described for assay optimization (See: col. 7, line 16 to col. 8). Conditions which require optimization of specific and non-specific hybridization include the concentration of polymer, the temperature of hybridization, the salt concentration, and the presence or absence of unrelated nucleic acid (See: col. 8, lines 15–18).

Shuber does not expressly suggest performing a probe-based hybridization assay on an electrostatically immobilized nucleic acid and specifically does not describe or teach the analysis of electrostatically immobilized nucleic acid using a non-nucleotide probe such as a peptide nucleic acid. Furthermore, Shuber does not suggest, disclose or teach any advantages, such the ability to work within a broad range of assay conditions, of performing a peptide nucleic acid-based analysis of nucleic acid electrostatically immobilized to a matrix.

Pluskal et al. describe a comparison of DNA and peptide nucleic acid (PNA) probe-based analysis of nucleic acid which has been irreversibly crosslinked to charged nylon membrane (See: Pluskal et al., American Society for Biochemistry, 85th Annual Meeting, Washington, D.C., May 1994). Pluskal et al. teach that while PNA probes can be used to detect the irreversibly immobilized nucleic acid under standard hybridization conditions, PNA works very well under highly stringent hybridization and washing conditions (See: The Section Entitled "Discussion"). Pluskal et al. also teach the use of 1% BSA as a blocking agent to reduce non-specific binding of the probe to the membrane (See: Section Entitled "Discussion"). Because the nucleic acid of Pluskal et al. has been irreversibly crosslinked to the nylon membrane, highly stringent hybridization and washing conditions can be applied to the membrane without reducing the amount of target nucleic acid present on the support and available for analysis. Pluskal et al. therefore demonstrate a rationale for irreversibly linking the nucleic acid to be analyzed to the support and using a blocking agent when performing a PNA probe-based analysis using a charged nylon membrane.

Methods for the protection of nucleic acid sequences from nuclease degradation/digestion by hybridizing a nucleic acid analog thereto have been described (See: Stanley et al.; U.S. Pat. No. 5,861,250). The methods and compositions described in Stanley et al. are particularly well suited for "cleaning up" a nucleic acid sample by degrading all nucleic acid present except the target sequence, . . . " (See: Stanley et al. at col. 7, lines 14–18). Stanley et al. describe several means for separating hybridized nucleic acid analog from non-hybridized nucleic acid analog, including ion exchange chromatography (See: Col. 6, lines 62–64), but they do not describe the simple electrostatic immobilization of the target sequence or nucleic acid analog/target sequence complex to a matrix as means to separate the hybridized nucleic acid analog from non-hybridized nucleic acid analog or otherwise separate the nucleic acid analog/target sequence complex from the other components of a sample.

Methods and apparatus for the electroactive transport and fixation of nucleic acids for analysis have been described (See: Heller et al., U.S. Pat. No. 5,849,486). However, this invention requires highly sophisticated instrumentation and devices to transport, fix and/or analyze a sample.

Though van den Engh does not discuss the detection of complex macromolecules such as nucleic acids, fluorescent reporter beads and methods for detecting the presence or determining the concentration of fluid bulk analytes such as pH, oxygen saturation and ion content are known in the art (See: van den Engh et al., U.S. Pat. No. 5,747,349). According to van den Engh, "Reporter beads are added to a fluid sample and the analyte concentration is determined by measuring fluorescence of individual beads, for example in a flow cytometer" (See: Abstract of U.S. Pat. No. 5,747, 349). The beads of van den Engh et al. comprise a substrate bead having a plurality of fluorescent reporter molecules immobilized thereon wherein the fluorescent reporter molecules comprise a fluorescent molecule whose fluorescent properties are a function of the concentration of the particular analyte whose presence or concentration is to be determined (See: U.S. Pat. No. 5,747,349 at col. 3, lns. 29–46). Thus, the beads of van den Engh are inherently fluorescent and not the analytes or derivatives thereof.

Recently, compositions containing at least one bead conjugated to a solid support and further conjugated to at least one macromolecule have been described in the art (See: Lough et al., PCT/US97/20194). Claimed advantages of Lough et al. include increased surface area for the immobilization of biological particles or macromolecules as compared to flat surfaces as well as the ability to use one chemistry for the immobilization of the macromolecule to the bead and a different chemistry to attach the bead to the support. Lough et al. define macromolecules to include nucleic acids (See: p. 7, Ins. 10–17) and further define peptide nucleic acids (PNA) as being analogs of nucleic acids (See: p. 8, Ins. 4–9). The invention of Lough et al. is primarily directed to analysis of immobilized macromolecules. Curiously however, a probe-based assay is not described as a detection method but rather Lough et al. focus on direct analysis of the immobilized macromolecule be means such as MALDI-TOF mass spectrometry. Apart from apparently being considered by Lough et al. to be an analog of a nucleic acid, PNA is not otherwise mentioned in the disclosure and no examples are provided which demonstrate that PNA is suitable for the practice of the invention.

Despite its name, Peptide Nucleic Acid (PNA) is neither a peptide, a nucleic acid nor is it an acid. Peptide Nucleic Acid (PNA) is a non-naturally occurring polyamide which can hybridize to nucleic acid (DNA and RNA) with sequence specificity (See: U.S. Pat. Nos. 5,539,082, 5,527, 675, 5,623,049, 5,714,331, 5,736,336, 5,773,571 or 5,786, 461 as well as Egholm et al., Nature 365: 566–568 (1993)). Being a non-naturally occurring molecule, unmodified PNA is not known to be a substrate for the enzymes which are known to degrade peptides or nucleic acids. Therefore, PNA should be stable in biological samples, as well as have a long shelf-life. Unlike nucleic acid hybridization which is very dependent on ionic strength, the hybridization of a PNA with a nucleic acid is fairly independent of ionic strength and is favored at low ionic strength, conditions which strongly disfavor the hybridization of nucleic acid to nucleic acid (Egholm et al., Nature, at p. 567). The effect of ionic strength on the stability and conformation of PNA complexes has been extensively investigated (Tomac et al., J. Am. Chem. Soc. 118:55 44–5552 (1996)). Sequence discrimination is more efficient for PNA recognizing DNA than for DNA recognizing DNA (Egholm et al., Nature, at p. 566). However, the advantages in point mutation discrimination with PNA probes, as compared with DNA probes, in a hybridization assay, appears to be somewhat sequence dependent (Nielsen et al., Anti-Cancer Drug Design 8:53–65, (1993) and Weiler et al., Nucl. Acids Res. 25: 2792–2799 (1997)).

Because the nucleic acids of a complex sample, such as a cell lysate or PCR reaction mixture, can be concentrated and also partially purified by immobilization to supports, probe-based hybridization assays could be simplified if the presence of a target nucleic acid could be specifically detected while the target nucleic acid remained support bound; particularly if the conditions for the treatment, analysis and/or detection of the target sequence were operable within a broad range so that assay conditions did not require substantial and laborious optimization. The ability to perform such analyses using a flow cytometer, an array, a nuclease digestion/protection assay, a line assay, a self-indicating assay or in some combination of these assay formats would be particularly beneficial.

SUMMARY OF THE INVENTION

This invention pertains to methods, kits and compositions suitable for the detection, identification and/or quantitation of nucleic acids which are electrostatically immobilized to matrices using non-nucleotide probes which sequence specifically hybridize to one or more target sequences of the nucleic acid but do not otherwise substantially interact with the matrix. Once the nucleic acid is immobilized, the detectable non-nucleotide probe/target sequence complex, formed before or after the immobilization of the nucleic acid, can be detected, identified or quantitated under a wide range of assay conditions as a means to detect, identify or quantitate the target sequence in the sample. Because it is reversibly bound, the non-nudeotide probe/target sequence can optionally be removed from the matrix for detecting, identifying or quantitating the target sequence in the sample. Because the non-nucleotide probe/target sequence is protected against degradation, it is another advantage of this invention that the sample can be treated with enzymes which degrade sample components, either before or after the nucleic acid is bound to the matrix, in order to "clean up" the sample (e.g. a complex biological sample such as a cell lysate) and thereby improve the detection, identification or quantitation of the target sequence in the sample. Consequently, the methods, kits and compositions of this invention have substantial advantages over all previously known or described methods, kits or compositions because they facilitate the simple processing and/or analysis of samples, and particularly complex biological samples, under a wide range of assay conditions.

In one embodiment, this invention is related to a composition comprising a nucleic acid, having at least one target sequence, which is electrostatically bound to a matrix under suitable electrostatic binding conditions. The composition further comprises a detectable, but not necessarily labeled, non-nucleotide probe having a probing nucleobase sequence which is sequence specifically hybridized to at least a portion of the target sequence.

In another embodiment, this invention pertains to methods for the detection, identification or quantitation of a target sequence in a sample containing nucleic acid. One exemplary method comprises contacting a sample with a matrix and at least one non-nucleotide probe wherein the nucleic acid in the sample will electrostatically bind to the matrix under suitable electrostatic binding conditions. Additionally, the non-nucleotide probe will hybridize, under suitable hybridization conditions, to at least a portion of the target sequence, if present in the sample. The method further comprises detecting, identifying or quantitating the non-nucleotide probe/target sequence hybrid as a means to detect, identify or quantitate the target sequence in the sample.

In still another embodiment, this invention pertains to multiplex methods for the detection, identification or quantitation of two or more target sequences of one or more nucleic acid molecules which may be present in the same sample. One exemplary method comprises contacting a sample with a matrix and two or more independently detectable non-nucleotide probes wherein the nucleic acid present in the sample will electrostatically bind to the matrix under suitable electrostatic binding conditions. Additionally, the two or more independently detectable non-nucleotide probes will hybridize, under suitable hybridization conditions, to at least a portion of the target sequences with which each probe is designed to hybridize if present in the nucleic acid of the sample. Consequently, if a particular target sequence is electrostatically immobilized to the matrix, the independently detectable non-nucleotide probe designed to hybridized to that particular target sequence will become concentrated on the matrix and be available for detection. Therefore, the method further comprises detecting, identifying or quantitating each unique independently detectable non-nucleotide probe/target sequence hybrid which is electrostatically bound to said matrix as a means to detect, identify or quantitate each unique target sequence sought to be detected in the sample and in the same assay. Optionally, the unique independently detectable non-nucleotide probe/target sequence hybrid is released from the matrix by adjustment of conditions outside the range required for electrostatic binding and thereby facilitates detection of the unbound non-nucleotide probe/target sequence hybrid, or just the detectable probe, as the means to detect, identify or quantitate the target sequence in the sample.

In still a further embodiment, this invention takes advantage of the stability of nucleic acid analog/nucleic acid complexes (See: Stanley et al.; U.S. Pat. No. 5,861,250) to thereby further improve assay performance and/or otherwise decrease the labor or complexity of sample preparation. One exemplary method comprises contacting the sample with at least one non-nucleotide probe wherein the non-nucleotide probe will hybridize, under suitable hybridization conditions, to at least a portion of the target sequence if present in the sample. The sample is also contacted with a matrix wherein the nucleic acid molecule will electrostatically bind to a matrix under suitable electrostatic binding conditions. Either before or after immobilization to the matrix, the sample containing the non-nucleotide probe/target sequence complex is contacted with one or more enzymes capable degrading sample contaminants possibly including the nucleic acid molecule but not the non-nucleotide probe/target sequence complex. The method further comprises detecting, identifying or quantitating the non-nucleotide probe/target sequence hybrid as a means to detect, identify or quantitate the target sequence in the sample. Optionally, the detectable non-nucleotide probe/target sequence hybrid is released from the matrix by adjustment of conditions outside the range required for electrostatic binding and thereby facilitates detection of the unbound non-nucleotide probe/target sequence hybrid, or just the detectable probe, as the means to detect, identify or quantitate the target sequence in the sample.

In yet another embodiment, this invention relates to a method for the detection, identification or quantitation of a target sequence of a nucleic acid molecule electrostatically immobilized at a location on an array wherein the array comprises nucleic acid molecules electrostatically bound at unique locations. One exemplary method comprises contacting the array with at least one non-nucleotide probe, wherein the non-nucleotide probe will hybridize, under suitable hybridization conditions, to at least a portion of the target sequence if present on the array. The non-nucleotide probe/target sequence complex electrostatically bound at a location on said array is then detected, identified or quantitated as the means to determine the presence, absence or amount of target sequence present at said array location. It is an advantage of the invention that one or more enzymes capable of degrading sample contaminants including the nucleic acid target molecule but not the non-nucleotide probe/target sequence complex, can also be added before analysis of the array to thereby improve the performance of the array assay by degrading sample contaminants which might otherwise lead to false positive results. Optionally, the detectable non-nucleotide probe/target sequence hybrids can be released from the matrix by adjustment of conditions outside the range required for electrostatic binding and thereby facilitates detection of the unbound non-nucleotide probe/target sequence hybrid, or just the detectable probe, as the means to detect, identify or quantitate target sequence in the sample. If the non-nucleotide probes are independently detectable, the analysis of the matrix can proceed in a multiplex format.

In yet a further embodiment, this invention is directed to a method for the detection, identification or quantitation of a target sequence of a nucleic acid molecule which may be present in any of two or more samples of interest. The method comprises mixing each of the two or more samples of interest with at least one non-nucleotide probe, under suitable hybridization conditions. Next a matrix is contacted, under suitable electrostatic binding conditions, with at least a portion of each of the two or more samples to thereby electrostatically immobilize the nucleic acid components of each sample to the matrix, each at a unique location, and thereby create a matrix array of samples. The non-nucleotide probe/target sequence complex electrostatically bound at a location on said array is then detected, identified or quantitated as the means to determine the presence, absence or amount of target sequence present at said array location. It is an advantage of the invention that one or more enzymes capable of degrading sample contaminants including the nucleic acid target molecule but not the non-nucleotide probe/target sequence complex, can also be added before analysis of the array to thereby improve the performance of the array assay by degrading sample contaminants which might otherwise lead to false positive results. Optionally, the detectable non-nucleotide probe/target sequence hybrids can be released from the matrix by adjustment of conditions outside the range required for electrostatic binding and thereby facilitates detection of the unbound non-nucleotide probe/target sequence hybrid, or just the detectable probe, as the means to detect, identify or quantitate target sequence in the sample. If the non-nucleotide probes are independently detectable, the analysis of the matrix can proceed in a multiplex format.

In yet another embodiment, this invention is directed to kits suitable for performing an assay which detects the presence, absence or number of target sequences present in a sample. The kits of this invention comprise a matrix and one or more non-nucleotide probes and optionally one or more other reagents or compositions which are selected to perform an assay of this invention or otherwise simplify the performance of an assay used to detect, identify or quantitate a target sequence in a sample.

The compositions, methods and kits of this invention are particularly useful for the detection, identification and/or enumeration of bacteria and eucarya (e.g. pathogens) in food, beverages, water, pharmaceutical products, personal care products, dairy products or environmental samples. The analysis of preferred non-limiting beverages include soda, bottled water, fruit juice, beer, wine or liquor products. Suitable compositions, methods and kits will be particularly useful for the analysis of raw materials, equipment, products or processes used to manufacture or store food, beverages, water, pharmaceutical products, personal care products dairy products or environmental samples.

Additionally, the compositions, methods and kits of this invention are particularly useful for the detection of bacteria and eucarya (e.g. pathogens) in clinical samples and clinical environments. Suitable compositions, methods and kits will be particularly useful for the analysis of clinical specimens, equipment, fixtures or products used to treat humans or animals.

BRIEF DESCRIPTION OF THE DRAWINGS

FIG. 5 is a computer generated negative of an image of a photograph of tubes from an experiment used to determine the range of ionic strength suitable for electrostatic immobilization of probes, target nucleic acids and probe/target nucleic acid complexes.

DETAILED DESCRIPTION OF THE INVENTION

Figure 1A:
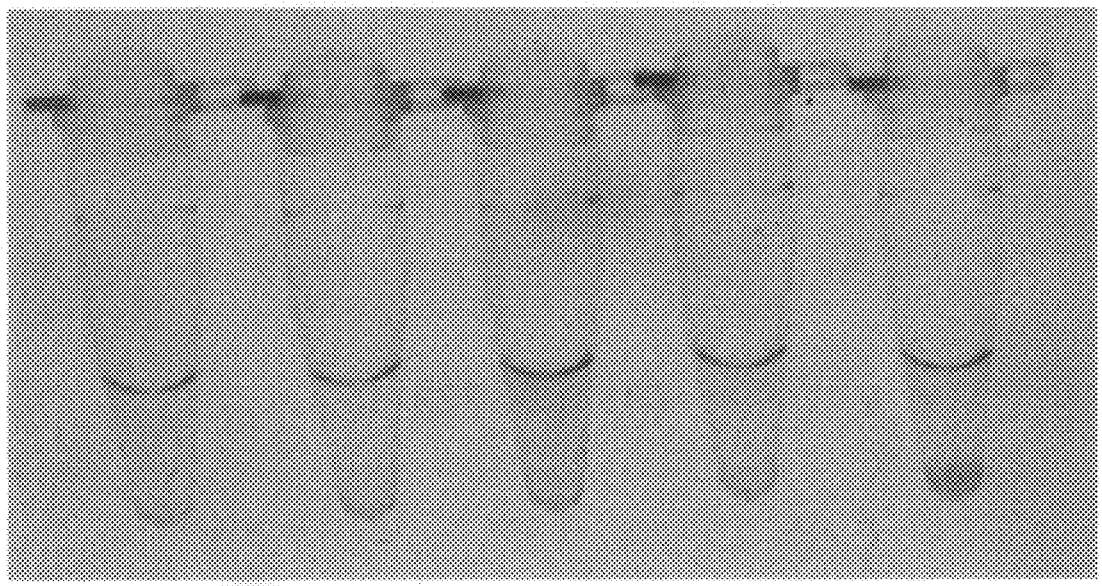
FIGS. 1A and 1B are computer generated negatives of the image of a photograph of tubes from an experiment using PCR to amplify a nucleic acid comprising a target sequence to which a Linear Beacon hybridizes to generate detectable signal.

1. Definitions a. As used herein, the term "nucleobase" shall include those naturally occurring and those non-naturally occurring heterocyclic moieties commonly known to those who utilize nucleic acid technology or utilize peptide nucleic acid technology to thereby generate polymers which can sequence specifically hybridize to nucleic acids.

b. As used herein, the term "nucleobase sequence" is any segment of a polymer which comprises nucleobase containing subunits. Non-inmiting examples of suitable polymers or polymers segments include oligonucleotides, oligoribonucleotides, peptide nucleic acids and analogs or chimeras thereof.

c. As used herein, the term "target sequence" is the nucleobase sequence of a nucleic acid molecule of interest which is sought to be detected in an assay and to which at least a portion of the probing nucleobase sequence of the non-nucleotide probe is intended to hybridize. The target sequence may comprise a subset of the nucleic acid molecule or may be the entire nucleic acid molecule of interest.

d. As used herein, the terms "label" and "detectable moiety" shall be interchangeable and shall refer to moieties which can be attached to a non-nucleotide probe, antibody or antibody fragment to thereby render the non-nucleotide probe, antibody or antibody fragment detectable by an instrument or method.

e. As used herein, the term "non-nucleotide probe" shall mean a polymer which is not a polynucleotide but which comprises a probing nucleobase sequence which is designed to hybridize to at least a portion of the target sequence. A preferred non-limiting example of a non-nucleotide probe is a peptide nucleic acid (PNA) probe.

f. As used herein, the term "peptide nucleic acid" or "PNA" shall be defined as a non-nucleotide polymer comprising two or more PNA subunits (residues), including any of the compounds referred to or claimed as peptide nucleic acids in U.S. Pat. Nos. 5,539,082, 5,527,675, 5,623,049, 5,714,331, 5,736,336, 5,773,571 or 5,786,461 (all of which are herein incorporated by reference). The term "peptide nucleic acid" or "PNA" shall also apply to polymers comprising two or more subunits of those nucleic acid mimics described in the following publications: Diderichsen et al., *Tett. Lett.* 37: 475–478 (1996); Fujii et al., *Bioorg. Med. Chem. Lett.* 7: 637–627 (1997); Jordan et al., *Bioorg. Med. Chem. Lett.* 7: 687–690 (1997); Krotz et al., *Tett. Lett.* 36: 6941–6944 (1995); Lagriffoul et al., *Bioorg. Med. Chem. Lett.* 4: 1081–1082 (1994); Lowe et al., *J. Chem. Soc. Perkin Trans.* 1, (1997) 1: 539–546; Lowe et al., *J. Chem. Soc. Perkin Trans.* 11: 547–554 (1997); Lowe et al., *J. Chem. Soc. Perkin Trans.* 1 1:5 55–560 (1997); Petersen et al., *Bioorg. Med. Chem. Lett.* 6: 793–796 (1996); Diederichsen, U., *Bioorganic & Med. Chem. Lett.,* 8: 165–168 (1998); Cantin et al., *Tett. Lett.,* 38: 4211–4214 (1997); Ciapetti et al., *Tetrahedron,* 53: 1167–1176 (1997); Lagriffoule et al., *Chem. Eur. J.,* 3: 912–919 (1997) and WIPO patent application WO96/04000 by Shah et al. and entitled "Peptide-based nucleic acid mimics (PENAMs)".

In preferred embodiments, a PNA is a polymer comprising two or more subunits of the formula:

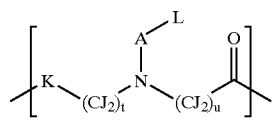

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; $—(CJ_2)_s—$ and a group of the formula; $—(CJ_2)_sC(O)—$, wherein, J is defined above and each s is an whole number from one to five. The whole number t is 1 or 2 and the whole number u is 1 or 2. Each L is the same or different and is independently selected from the group consisting of J, adenine, cytosine, guanine, thymine, uridine, 5-methylcytosine, 2-ariunopurine, 2-amino-6 chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

2. Description
I. General
Probes

The probes used for the practice of this invention are non-nucleotide probes which at a minimum comprise a probing nucleobase sequence designed to hybridize to at least a portion of a target sequence sought to be detected in a probe-based hybridization assay. The non-nucleotide probes comprise a sufficiently neutral or positively charged backbone such that they exhibit little or no affinity for the matrix under a broad range of assay conditions including substantial variations in pH, buffer ionic strength, detergent concentration and/or chemical denaturant concentration. This broad range of conditions under which little or no interaction occurs between the non-nucleotide probe and the matrix is a substantial advantage over the previous methods such as those of Arnold et al. (U.S. Pat. No. 5,599,667) which required substantial. condition optimization to achieve discrimination of between the non-specific binding of the nucleotide probe and the target nucleic acid (or nucleotide probe/target nucleic acid complex) to the matrix.

It is still another advantage of this invention that substantial changes in the ionic strength of the assay have little effect on the Tm of the non-nucleotide probe/target sequence hybrid (See: (Egholn et al *Nature* 365: 566–568 (1993) and Tomac et al., *J. Am. Chem. Soc.* 118:55 44–5552 (1996)). Consequently, this lack of sensitivity of the hybrid to changes in ionic strength also broadens the range of possible assay conditions.

The non-nucleotide probes may be labeled with a detectable moiety or may be unlabeled provided however that the non-nucleotide probe/target sequence hybrid is detectable when the probe is unlabeled. The preferred non-nucleotide probes are PNA probes. Preferred labeled non-nucleotide probes are non-nucleotide "Beacon" probes (See: the Section entitled "Non-Nucleotide "Beacon" Probes, below) because they are self-indicating. By self-indicating we mean that the probes change detectable properties upon hybridization to a target sequence and thereby reduce or eliminate the requirement for the removal of excess probe. In one embodiment, the self-indicating probes of this invention will rely on a change in fluorescence which can be observed with the eye or otherwise detected and/or quantitated with a fluorescence instrument.

Because it is an important feature of this invention that the non-nucleotide probes do not substantially interact with the matrix, the non-nucleotide probes of this invention may also be designed, by appropriate modification, to have a particular net charge. For example, certain choices of labels might cause the non-nucleotide probe to have a net negative charge (See: Example 9). However, the net charge of the probe can be changed by adding one or more positively charged moieties, such as by linking one or more of compounds 7 or 8 as described by Gildea et al., *Tett. Lett.* 39: 7255–7258 (1998). By the alteration of net charge, the probes can be designed to have any combination of desired labels and still not exhibit an affinity for the matrix.

Unlabeled Non-Nucleotide Probes

The non-nucleotide probes used for the practice of this invention need not be labeled with a detectable moiety to be operable within the methods of this invention. When using the non-nucleotide probes it is possible to detect the non-nucleotide probe/nucleic acid complex formed by hybridization of the probing nucleobase sequence of the probe to the target sequence using an antibody to the non-nucleotide probe/nucleic acid hybrid (complex). As a non-lirniting example, a PNA/nucleic acid complex could be detected using an antibody which specifically interacts with the complex under suitable antibody binding conditions. Suitable antibodies to PNA/nucleic acid complexes and methods for their preparation and use are described in WIPO Patent Application WO95/17430 as well as U.S. Pat. No. 5,612, 458, herein incorporated by reference.

The antibody/PNA/nucleic acid complex formed by interaction of the α-PNA/nucleic acid antibody with the PNA/nucleic acid complex can be detected by several methods. For example, the α-PNA/nucleic acid antibody could be labeled with a detectable moiety. Suitable detectable moieties (labels) are described herein. Thus, the presence, absence or quantity of the detectable moiety is correlated with the presence, absence or quantity of the antibody/PNA/nucleic acid complex and the target sequence sought to be identified. Alternatively, the antibody/PNA/nucleic acid complex is detected using a secondary antibody which is labeled with a detectable moiety. Typically the secondary antibody specifically binds to the α-PNA/nucleic acid antibody under suitable antibody binding conditions. Thus, the presence, absence or quantity of the detectable moiety is correlated with the presence, absence or quantity of the antibody/antibody/PNA/nucleic acid complex and the target sequence sought to be identified. As used herein, the term antibody shall include antibody fragments which specifically bind to other antibodies or other antibody fragments.

Probing Nucleobase Sequence

The probing nucleobase sequence of a non-nucleotide probe used for the practice of this invention is the sequence recognition portion of the construct. Therefore, the probing nucleobase sequence is designed to hybridize to at least a portion of the target sequence since it may be preferable to use two or more probes designed to hybridize to the entire target sequence (See for example: European Patent Application entitled "Method of identifying a nucleic acid using triple helix formation of adjacently annealed probes"; EP-A-849-363 as well as WIPO patent application No. WO99/55916 entitled "Methods, Kits and Compositions for Detecting and Quantitating Target Sequencers). Preferably, the probing nucleobase sequence hybridizes to the entire target sequence. Detection of non-nucleotide probe hybridization to the target sequence can be correlated with the presence, absence or amount of target sequence present in a sample.

The probing nucleobase sequence of a non-nucleotide probe will preferably be exactly complementary to all or a portion of the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., *Nature Biotechnology* 15:331–335 (1997)).

With due consideration to the requirements of a non-nucleotide probe for the assay format chosen and the target sequence sought to be detected, the probing nucleobase sequence will generally be chosen such that a stable complex is formed with all or a portion of the target sequence, under suitable hybridization conditions. Generally however, the non-nucleotide probes suitable for the practice of this invention, will generally have a probing nucleobase sequence in the range of 5–50 subunits. More preferably, the probing nucleobase sequence will be in the range of 7–25 subunits in length and most preferably in the range of 12–20 subunits in length.

PNA Synthesis

Methods for the chemical assembly of PNAs are well known (See: U.S. Pat. Nos. 5,539,082, 5,527,675, 5,623,049, 5,714,331, 5,736,336, 5,773,571 or 5,786,571, herein incorporated by reference). Chemicals and instrumentation for the support bound automated chemical assembly of peptide nucleic acids are now commercially available. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling

Labeling of a PNA is analogous to peptide labeling. Because the synthetic chemistry of assembly is essentially the same, any method commonly used to label a peptide can usually be adapted for use in labeling a PNA. Thus, PNAs may be labeled with numerous detectable moieties. Generally, any detectable moiety which can be linked to a nucleic acid or peptide can be linked to a PNA.

Typically, the N-terminus of the PNA is labeled by reaction with a moiety having a carboxylic acid group or activated carboxylic acid group. One or more spacer moieties can be introduced between the labeled moiety and the PNA oligomer. Generally, the spacer moiety is incorporated prior to performing the labeling reaction. However, the spacer may be embedded within the label and thereby be incorporated during the labeling reaction. Specialized reagents can be attached to the PNA. For example, a terminal arylamine moiety can be generated by condensing a suitably protected 4-aminobenzoic acid derivative with the amino terminus of the PNA oligomer.

In one embodiment, the C-terminal end of the PNA is labeled by first condensing a labeled moiety with the support upon which the labeled PNA is to be assembled. Next, the first synthon of the PNA is condensed with the labeled moiety. Alternatively, one or more spacer moieties can be introduced between the labeled moiety and the PNA oligomer (e.g. 8-amino-3,6-dioxaoctanoic acid). After the PNA is completely assembled and labeled, the PNA is cleaved from the support, deprotected and purified using standard methodologies.

For example, the labeled moiety could be a lysine derivative wherein the E-amino group is labeled with a detectable moiety such as 5(6)-carboxyfluorescein. Alternatively, the labeled moiety could be a lysine derivative wherein, the ε-amino group is derivatized with a 4-aminobenzoic acid moiety (e.g. 4-(N-(tert-butyloxycarbonyl)-aminobenzamide). Condensation of the lysine derivative with the support would be accomplished using standard condensation (peptide) chemistry. The α-amino group of the lysine derivative could then be deprotected and the PNA assembly initiated by condensation of the first PNA synthon with the α-amino group of the lysine amino acid. After complete assembly, the PNA oligomer would then be cleaved from the support, deprotected and purified using well known methodologies.

Alternatively, a functional group on the assembled, or partially assembled, polymer is labeled with a donor or acceptor moiety (e.g. a PNA Molecular Beacon or a Linear Beacon) while it is still support bound. This method requires that an appropriate protecting group be incorporated into the oligomer to thereby yield a reactive functional to which the donor or acceptor moiety is linked but has the advantage that the label (e.g. a fluorophore) can be attached to any position within the polymer including within the probing nucleobase sequence. For example, the ε-amino group of a lysine could be protected with a 4-methyl-triphenylmethyl (Mtt), a 4-methoxy-triphenylmethyl (MMT) or a 4,4'-dimethoxytriphenylmethyl (DMT) protecting group. The Mtt, MMT or DMT groups can be removed from PNA (assembled using commercially available Fmoc PNA monomers and polystyrene support having a PAL linker; PerSeptive Biosystems, Inc., Framingham, Mass.) by treatment of the resin under mildly acidic conditions. Consequently, the donor or acceptor moiety can then be condensed with the ε-amino group of the lysine amino acid. After complete assembly and labeling, the polymer is then cleaved from the support, deprotected and purified using well known methodologies.

Alternatively, a label (including one of the donor or acceptor moiety wherein the other of the donor or acceptor moiety is linked to the PNA during assembly) is attached to the PNA after it is fully assembled, cleaved from the support and optionally purified. This method is preferable where the label is incompatible with the cleavage, deprotection or purification regimes commonly used to manufacture PNA. By this method, the PNA will generally be labeled in solution by the reaction of a functional group on the PNA and a functional group on the label. Those of ordinary skill in the art will recognize that the composition of the coupling solution will depend on the nature of PNA and the label. The solution may comprise organic solvent, water or any combination thereof. Generally, the organic solvent will be a polar non-nucleophillc solvent. Non-limiting examples of suitable organic solvents include acetonitrile, tetrahydrofuran, dioxane and N,N'-dimethylformamide.

Generally the functional group on the PNA will be an amine and the functional group on the label will be a carboxylic acid or activated carboxylic acid. Non-lnniting examples of activated carboxylic acid functional groups include N-hydroxysuccinimidyl esters. If the label is an enzyme, preferably the amine on the PNA will be an arylamine. In aqueous solutions, the carboxylic acid group of either of the PNA or label (depending on the nature of the components chosen) can be activated with a water soluble carbodiimide. The reagent, 1-(3 -dimethylamninopropyl)-3-ethylcarbodiimnide hydrochloride (EDC), is a commercially available reagent sold specifically for aqueous amide forming condensation reactions.

Generally, the pH of aqueous solutions will be modulated with a buffer during the condensation reaction. Preferably, the pH during the condensation is in the range of 4–10. When an arylamine is condensed with the carboxylic acid, preferably the pH is in the range of 4–7. When an alkylamine is condensed with a carboxylic acid, preferably the pH is in the range of 7–10. Generally, the basicity of non-aqueous reactions will be modulated by the addition of non-nucleophilic organic bases. Non-limiting examples of suitable bases include N-methylmorpholine, triethylamine and N,N-diisopropylethylamine. Alternatively, the pH is modulated using biological buffers such as (N-[2-hydroxyethyl] piperazine-N'-[2-ethanesulfonic acid) (HEPES) or 4-morpholineethane-sulfonic acid (MES) or inorganic buffers such as sodium bicarbonate.

Exemplary Labels

Numerous detectable moieties may be used for the practice of this invention. Suitable detectable or independently detectable moieties will be chosen to be compatible with the assay to be performed. Generally, the labels will be chosen so that the label pair is neutral or positively charged so that when labeled, the non-nucleotide probe does not exhibit a substantial affinity for the matrix. Alternatively, the probe can be designed to incorporate charges (generally positive charges) so that even if the net charge of the labels is negative, the labeled probe is neutral or positively charged and therefore exhibits little or no affinity for the matrix.

Non-limiting examples of detectable moieties (labels) suitable for use in the practice of this invention would include dextran conjugates, a branched nucleic acid detection system, chromophores, fluorochromes, spin labels, radioisotopes, mass labels, enzymes, haptens and chemiluminescent compounds. Preferred labeling reagents will be supplied as carboxylic acids or as the N-hydroxysuccinidyl esters of carboxylic acids. Numerous amine reactive labeling reagents are commercially available (as for example from Molecular Probes, Eugene, Oreg.). Preferred fluorochromes (fluorophores) include 5(6)-carboxyfluorescein (Flu), 6-((7-amino-4-methylcoumarin-3-acetyl)amino) hexanoic acid (Cou), 5(and 6)-carboxy-X-rhodamine (Rox), Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 3, 3.5, 5 and 5.5 are available as NHS esters from Amersham, Arlington Heights, Ill.) or the Alexa dye series (Molecular Probes). Preferred haptens include 5(6)-carboxyfluorescein, 2,4-dinitrophenyl, digoxigenin, and biotin. Preferred enzymes include soybean peroxidase, alkaline phosphatase and horseradish peroxidase. Other suitable labeling reagents and preferred methods of attachment would be recognized by those of ordinary skill in the art of PNA synthesis.

Non-Nucleotide "Beacon" Probes

The labels attached to the non-nucleotide "Beacon" probes comprise a set (hereinafter "Beacon Set(s)") of energy transfer moieties comprising at least one energy transfer donor and at least one energy transfer acceptor moiety. Typically, the Beacon Set will include a single donor moiety and a single acceptor moiety. Nevertheless, a Beacon Set may contain more than one donor moiety and/or more than one acceptor moiety. The donor and acceptor moieties operate such that one or more acceptor moieties accepts energy transferred from the one or more donor moieties or otherwise quench signal from the donor moiety or moieties. Though the previously listed fluorophores (with suitable spectral properties) might also operate as energy transfer acceptors, preferably, the acceptor moiety is a quencher moiety. Preferably, the quencher moiety is a non-fluorescent aromatic or heteroaromatic moiety. The preferred quencher moiety is 4-((-4-(dimethylamino)phenyl)azo) benzoic acid (dabcyl).

Transfer of energy between donor and acceptor moieties of a non-nucleotide "Beacon" probe may occur through collision of the closely associated moieties of a Beacon Set or through a nonradiative process such as fluorescence resonance energy transfer (FRET). For FRET to occur, transfer of energy between donor and acceptor moieties of a Beacon Set requires that the moieties be close in space and that the emission spectrum of a donor(s) have substantial overlap with the absorption spectrum of the acceptor(s) (See: Yaron et al. *Analytical Biochemistry*, 95: 228–235 (1979) and particularly page 232, col. 1 through page 234, col. 1). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry*, 95: 228–235 (1979) and particularly page 229, col. 1 through page 232, col. 1). This process is referred to as intramolecular collision since it is believed that quenching is caused by the direct contact of the donor and acceptor moieties (See: Yaron et al.).

(i) Linear Beacons

In a preferred embodiment, the non-nucleotide "Beacon" probe is a Linear Beacon as more fully described in co-pending patent application U.S. Ser. No. 09/179,162 and WIPO publication WO99/22018, entitled "Methods, Kits And Compositions Pertaining To Linear Beacons", herein incorporated by reference.

(ii) PNA Molecular Beacons

In a preferred embodiment, the non-nucleotide "Beacon" probe is a PNA Molecular Beacon as more fully described in co-pending patent application: U.S. Ser. No. 09/179,298 and WIPO publication WO99/21881, entitled "Methods, Kits And Compositions Pertaining To PNA Molecular Beacons", herein incorporated by reference.

Detecting Energy Transfer

Hybrid formation of a non-nucleotide "Beacon" probe with a target sequence can be monitored by measuring at least one physical property of at least one member of the Beacon Set which is detectably different when the hybridization complex is formed as compared with when the non-nucleotide "Beacon" probe exists in the absence of target sequence. We refer to this phenomenon as the self-indicating property of non-nucleotide "Beacon" probes. This change in detectable signal shall result from the change in efficiency of energy transfer between the donor and acceptor which results from hybridization of the non-nucleotide "Beacon" probes. Preferably, the means of detection will involve measuring fluorescence of a donor or acceptor fluorophore of a Beacon Set. Most preferably, the Beacon Set will comprise at least one donor fluorophore and at least one acceptor quencher such that the fluorescence of the donor fluorophore is will be used to detect, identify or quantitate hybridization of the non-nucleotide probe to the target sequence.

Other Non-Nucleotide Self-Indicating Probes

In another embodiment, the non-nucleotide probes of this invention are self-indicating probes of the type described in WIPO patent application WO97/45539. The self-indicating non-nucleotide probes described in WO97/45539 differ as compared with non-nucleotide "Beacon" probes primarily in that no quencher or acceptor moiety is present in the probes of WO97/45539. Preferably the probes of WO97/45539, as used in this invention, are appropriately labeled peptide nucleic acids.

Detectable and Independently Detectable Moieties/Multiplex Analysis

In preferred embodiments of this invention, a multiplex probe-based hybridization assay is performed. In a multiplex assay, numerous conditions of interest are simultaneously examined. Multiplex analysis relies on the ability to sort sample components or the data associated therewith, during or after the assay is completed. In preferred embodiments of the invention, distinct independently detectable moieties are used to label the different non-nucleotide probes of a set. The ability to differentiate between and/or quantitate each of the independently detectable moieties provides the means to multiplex a hybridization assay because the data which correlates with the hybridization of each of the distinctly (independently) labeled non-nucleotide probes to a target sequence can be correlated with the presence, absence or quantity of the target sequence sought to be detected in a sample. Consequently, the probe-based multiplex assays of this invention may be used to simultaneously detect the presence, absence or amount of each of two or more target sequences which may be present in the same sample and in the same assay.

Spacer/Linker Moieties

Generally, spacers are used to minimize the adverse effects that bulky labeling reagents might have on hybridization properties of probes. Linkers typically induce flexibility and randomness into the probe or otherwise link two or more nucleobase sequences of a probe. Preferred spacer/linker moieties for non-nucleotide probes used for the practice of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid) or alkyloxy diacids (e.g. diglycolic acid). Spacer/linker moieties may also incidentally or intentionally be constructed to improve the water solubility of the probe. The spacer/linker moieties may also be designed to enhance the solubility of the oligomer.

Preferably, a spacer/linker moiety comprises one or more linked compounds having the formula: $-Y-(O_m-(CW_2)_n)_o-Z-$. The group Y has the formula: a single bond, $-(CW_2)_p-$, $-C(O)(CW_2)_p-$, $-C(S)(CW_2)_p-$ and $-S(O_2)(CW_2)_p$. The group Z has the formula $NH, NR^2, S$ or $O$. Each W is independently $H, R^2, -OR^2, F, Cl, Br$ or $I$; wherein, each $R^2$ is independently selected from the group consisting of: $-CX_3$, $-CX_2CX_3$, $-CX_2CX_2CX_3$, $-CX_2CX(CX_3)_2$, and $-C(CX_3)_3$. Each X is independently $H, F, Cl, Br$ or $I$. Each m is independently 0 or 1. Each n, o and p are independently whole numbers from 0 to 10.

Linked Polymer

A linked polymer comprises two or more nucleobase sequences which are linked by a linker. The probes of this invention include linked polymers wherein the probing nucleobase sequence is linked to one or more additional peptide nucleic acid, peptide or enzyme molecules.

Hybridization Conditions/Stringency

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determing the effect of varying a single stringency factor. The same stringency factors can be modulated to thereby control the stringency of hybridization of non-nucleotide probes to target sequences, except that the hybridization of a PNA is fairly independent of ionic strength. Ionic strength will not likely be a substantial factor in the stringency of most non-nucleotide probes having a sufficiently neutral or positively charged backbone. Optimal stringency for an assay may be experimentally determined by examination of each stringency factor until the desired degree of discrimination is achieved.

Suitable Hybridization Conditions

Generally, the more closely related the background causing nucleic acid contaminants are to the target sequence, the more carefully stringency must be controlled. Blocking probes may also be used as a means to improve discrimination beyond the limits possible by mere optimization of stringency factors.[4] Suitable hybridization conditions will thus comprise conditions under which the desired degree of discrimination is achieved such that an assay generates an accurate (within the tolerance desired for the assay) and reproducible result. Aided by no more than routine experimentation, those of skill in the art will easily be able to determine appropriate hybridization conditions for performing an assay.

Blocking Probes

Blocking probes are non-nucleic acid or nucleic acid probes which can be used to suppress the binding of the probing nucleobase sequence of a probe to a hybridization site which is unrelated or closely related to the target sequence (See: Coull et al., PCT/US97/21845, a.k.a. WO98/24933). Generally, the blocking probes suppress the binding of the probing nucleobase sequence to closely related non-target sequences because the blocking probe hybridizes to the non-target sequence to form a more thermodynamically stable complex than is formed by hybridization between the probing nucleobase sequence and the non-target sequence. Thus, blocking probes are typically unlabeled probes used in an assay to thereby suppress non-specific signal. Because they are usually designed to hybridize to closely related non-target sequence sequences, typically a set of two or more blocking probes will be used in an assay to thereby suppress non-specific signal from non-target sequences which could be present and interfere with the performance of the assay.

Suitable Electrostatic Binding Conditions

It is an important feature of the present invention that the electrostatic binding conditions be chosen such that the non-nucleotide probe exhibit little or no affinity for the matrix as compared with nucleic acid components of the sample. The electrostatic immobilization of nucleic acids to matrices primarily involves the formation of salt pairs between the nucleic acid and the matrix. A salt pair comprises a charged species of the nucleic acid interacting with a counter charged species of the matrix to form an interaction which tends to stabilize the association of the nucleic acid to the matrix. Variable factors which will most affect electrostatic binding will involve modulation of one or both the pH and/or ionic strength. The pH is an important factor since it may affect the charge density on the matrix as well as the net charge of the nucleic acid. Similarly, ionic strength will affect salt pair stability since it is well known in the chromatographic arts that increasing ionic strength will destabilize the interactions formed between nucleic acids and anion exchange stationary phases. For the purposes of this invention, electrostatic binding conditions shall be conditions which allow for the reversible binding of the nucleic acid of interest to a matrix through salt pair formation.

Harmonization of Suitable Hybridization Conditions and Suitable Electrostatic Binding Conditions When employing the methods, kits and compositions of this invention, it is important to distinguish between suitable hybridization conditions, wherein sequence specific hybridization of a non-nucleotide probe to at target sequence is optimized, as compared with electrostatic binding conditions which simply refer to conditions under which the nucleic acid binds to the matrix but the non-nucleotide probe or probes do not exhibit a substantial affinity for the matrix. Typically, the electrostatic binding conditions will be chosen such that the non-nucleic probe is sufficiently neutral or positively charged. Because of the differences in the charges of the backbones of nucleic acid and non-nucleotide probes of this invention, there is a broad range of conditions within which the nucleic acid of interest binds to the matrix but the non-nucleotide probe or probes do not. This principle is exemplified in Example 13 wherein it is clear that the non-nucleotide probes do not interact with the matrix under any conditions examined but the most nearly equivalent nucleic acid probes can interact with the matrix under many of the conditions tested whether or not the target sequence is present in the sample.

Because it is an important feature of this invention that the non-nucleotide probe hybridize to a nucleic acid which is electrostatically bound to a matrix, it will be appreciated by one of skill in the art that hybridization conditions (stringency factors) and electrostatic binding conditions should be harmonized within the context of the assay to be performed. Since pH and ionic strength are factors to be considered in both stringency and electrostatic binding and since the electrostatic binding conditions are broad as compared with optimized stringency, it should always be possible to easily fix the electrostatic binding conditions and then optimize probe discrimination by modulation of other stringency factors. In this respect, the methods of this invention are far superior to current methods known in the art (e.g. Arnold et al, U.S. Pat. No. 5,599,667). Aided by no more than routine experimentation, those of skill in the art will easily be able to harmonize the electrostatic binding conditions and suitable hybridization conditions for performing an assay.

Matrices

Generally, the matrix is merely a scaffold which is potentially separable from the bulk fluid of the assay and which comprises charged functional groups to which the nucleic acid reversibly binds electrostatically. Typically, electrostatic binding occurs by salt pair formation between charged groups of the nucleic acid backbone and charged groups of the matrix. For binding nucleic acids, the primary interactions will most likely involve formation of a salt pair between the negatively charged phosphate groups of the nucleic acid phosphodiester backbone and positively charged functional groups of the matrix.

Non-limiting examples of suitable matrices include: polymers which are insoluble in water or mixtures of water and water soluble organic solvents; two and three dimensional surfaces such as a wall of a tube, a glass frit or a wafer; beaded supports such as magnetic beads, chromatographic packing supports, media and resins; porous beaded supports such as chromatographic packing supports, media and resins (e.g. anion exchange chromatography media), a cast polymer such as a membrane (e.g. polyvinylidene difluoride, Teflon, polyethylene, polypropylene or polysulfone); co-polymeric materials and gels (e.g. polyacrylamide or agarose). In a preferred embodiment, commercially available ion exchange chromatographic media, and particularly the beaded media, will be used as the matrix.

Matrix Shielding

In certain preferred embodiments, the matrix may be temporarily shielded from the assay components to thereby temporarily delay the electrostatic binding of nucleic acid components of the assay to the matrix. For example, it may be preferable to partially or wholly shield the matrix from assay components until a nucleic acid synthesis or amplification reaction is partially or substantially completed so as to not inhibit the synthesis or amplification (See for example: Example 12 of this specification).

Those of skill in the art will recognize that partitioning of reaction components may be obtained by preparing a reaction vessel having suitable compartments. Preferably however, the matrix will be shielded by the aid of a fluid which will serve as a temporary barrier until the reaction components are mixed. Thus, a preferable fluid will be a water miscible fluid which is viscous and/or dense as compared with water such that it does not readily blend with aqueous solutions until it is subjected to heating or physical agitation. It will be appreciated by those of skill in the art that a non-limiting example of such a fluid is glycerol.

Exemplary Assay Formats

The methods, kits and compositions of this invention substantially simplify the preparation and/or analysis of nucleic acids of interest. It is also an advantage that they are generally applicable to all types of samples and assay formats typically used for the analysis of nucleic acids.

Several non-limiting examples of preferred assay formats which have been tested are described below. These examples demonstrate the broad applicability of the methods, kits and compositions of this invention. Generally, the assay formats described below are not necessarily mutually exclusive and one or more can be combined for the analysis of a particular sample.

(i) Amplification Assay Formats

This invention is applicable to samples wherein the nucleic acid has been synthesized or amplified. Non-limiting examples of preferred nucleic acid synthesis or nucleic acid amplification reactions well known in the art include Polymerase Chain Reaction (PCR), Ligase Chain Reaction (LCR), Strand Displacement Amplification (SDA), Transcription-Mediated Amplification (TMA), Rolling Circle Amplification (RCA) and Q-beta replicase. When combined with non-nucleotide "Beacon" probes, these assay formats can be performed in a self-indicating format, including real-time as well as end-point determination when using a suitable instrument such as a Prism 7700 (PE Biosystems, Foster City, Calif.). In a self-indicating assay, once the components of the assay have been combined, there is no need to disturb contents of the assay to determine the result. Since the assay contents need not be disturbed to determine the result, there must be some detectable or measurable change which occurs and which can be observed or quantitated without physically manipulating the contents of the assay. Many self-indicating assays rely on a change in fluorescence which can be observed with the eye or otherwise detected and/or quantitated with a fluorescence instrument. Example 12 of this specification describes self-indicating PCR assays suitable for either real-time or end-point analysis.

(ii) Protection/Digestion Assays

Other preferred assays of this invention are directed to the detection of nucleic acids target sequences in samples; particularly within complex biological samples. Complex biological samples such as blood, urine, sputum and cell lysates typically require substantial processing in order to remove the bulk matter, such as protein, lipids, cellular debris, etc. which otherwise reduce the sensitivity and/or reliability of a probe-based hybridization assay. It has previously been demonstrated that nucleic acid analogs, such as PNA, can hybridize to a target sequence and thereby protect the nucleic acid target sequence from digestion/degradation by nucleases (See: Stanley et al.; U.S. Pat. No. 5,861,250). In this preferred assay format, one or more detectable non-nucleic acid probes which can protect the nucleic acid target from digestion/degradation, are hybridized to the one or more target sequences under suitable hybridization conditions. Preferably, the target sequence exists in a complex biological sample. After the non-nucleic acid probe has been hybridized to the nucleic acid target sequence, the sample is treated with one or more enzymes such as proteases and/or nucleases which degrade the sample components, possibly including the nucleic acid molecule of interest but not the non-nucleotide probe/target sequence complex. Because this treatment digests/degrades contaminating polymers and debris, this treatment reduces or eliminates the sample complexity and/or processing requirements normally associated with complex biological samples. Since the one or more non-nucleotide probe/target sequence hybrids, if present in the sample, are intact after the enzyme treatment, they can be concentrated on a matrix and detected as the means to detect, identify or quantitate the target sequence in the sample of interest. An example of this assay format is found in Example 14 of this specification. Optionally, the detectable non-nucleotide probe/target sequence hybrid is released from the matrix by adjustment of conditions outside the range required for electrostatic binding and thereby facilitates detection of the unbound non-nucleotide probe/target sequence hybrid, or just the detectable probe, as the means to detect, identify or quantitate the target sequence in the sample.

Advantageously, the presence of the matrix is not required for protecting the target sequence from degradation. Therefore, the matrix can either be present during the enzyme treatment or added after the enzyme treatment to thereby electrostatically immobilize the non-nucleotide probe/target sequence. In preferred embodiments, the nucleic acid analog is a non-nucleotide "Beacon" probe and the presence, absence or amount of self-indicating signal detected on the matrix is used to determine the presence, absence or amount of target sequence present in the sample or complex biological sample.

In a preferred embodiment of this assay, the assay temperature is adjusted and/or controlled so that imperfect hybrids are preferentially dissociated in order to achieve a higher degree of target sequence discrimination, including single point mutation discrimination. Generally, this involves adjusting the temperature of the assay to a point below the melting temperature of the non-nucleotide probe/target sequence hybrid so that non-nucleotide probe/non-target sequences are at least partially dissociated. Since the non-nucleotide probe/non-target sequence hybrids are generally less complementary as compared with the non-nucleotide probe/target sequence hybrids, the optimal assay temperature is typically within a fifteen degree range wherein this range is defined as five degrees above and ten degree below the melting temperature of the hybrid formed from the non-nucleotide probe and the non-target sequence. For example, if the non-nucleotide probe/non-target sequence sought to be discriminated in the assay has a melting temperature of 70° C., under assay conditions, the preferred range for adjusting the temperature of the assay would be between 75° C. (+5° C.) and 60° C. (−10° C.).

Dissociation of the non-nucleotide probe/non-target sequences makes the non-target sequences available for enzyme degradation since they are no longer protected. Though hybridization, particularly near the Tm, is an equilibrium process, destruction of the non-target sequence prevents reassociation of the non-nucleotide probe/non-target sequence hybrid and the generation of the non-specific signal associated therewith.

As previously stated, the assay formats described herein are not mutually exclusive to other assay formats. It is an important feature of this invention that the non-nucleotide probe/target sequence hybrid is reversibly bound to the matrix. Therefore the non-nucleotide probe/target sequence hybrid can be released from the matrix for subsequent analysis. Consequently, this Protection/Digestion Assay can also be used merely for sample preparation or as a confirmatory precursor assay to a secondary assay. For example, the Protection/Digestion Assays can be combined with other assay formats, such as for the analysis of arrays or for sample preparation, before performing a line assay or cytometric (flow or static) assay as described below.

(iii) Line Assays

Another preferred assay format useful for the practice of this invention is the line assay. A common line assay is a lateral flow assay. Many methods and devices for lateral flow assays are known (See: U.S. Pat. Nos. 5,916,521, 5,798,273, 5,770,460, 5,710,005, 5,415,994, 4,956,302 and 4,943,522, all of which are herein incorporated). A classic example of a lateral flow assay is a commercially available pregnancy test. In a classic pregnancy test, a sample of urine is applied to a spot on a lateral flow assay device. The lateral flow device comprises a fluid conducting matrix, such as a filter or membrane, which causes the fluid (e.g. urine) to passively flow (generally through capillary action) from the spot of application to the other end of the conducting matrix. Present within the lateral flow device (or otherwise added to the urine sample prior to application to the device) is a detectable antibody to the HCG hormone; said HCG hormone being present in the urine sample only if the subject is pregnant. As the urine flows laterally within the device, the HCG/antibody complex forms as the components interact. Also within the device is a line (or other geometric shape) of a substance (usually another antibody) to which the HCG/antibody complex will bind and thereby concentrate to produce a detectable signal.

Consequently, another embodiment of this invention contemplates a line or lateral flow assay for the detection of a nucleic acid target sequence. In the line assay of this invention, a line, lines or other geometric shape of matrix is spatially fixed on the device so that any non-nucleic acid probe/target sequence complexes present in a sample can be concentrated on the line (or other geometric shape) of the device as the sample (or sample components) flow past. Preferably the assay is a lateral flow assay. In the line assay of this invention, the detectable non-nucleic acid probe can be added to the sample before or after the target sequence is concentrated on the matrix of the line device. Consequently, the target sequence in the sample is determined by detecting, identifying or quantitating the non-nucleic acid probe/target sequence complex as concentrated on the line, lines or other geometric shape. Example 16 of this specification is an example of a line assay. Optionally, the non-nucleotide probe/target sequence hybrid is released from the matrix by adjustment of conditions outside the range required for electrostatic binding and thereby facilitates detection of the unbound non-nucleotide probe/target sequence hybrid, or just the detectable probe, as the means to detect, identify or quantitate the target sequence in the sample.

(iv) Array Assay Formats

In one embodiment, arrays are surfaces to which two or more samples of interest have been immobilized, each at a unique location. Arrays comprising nucleic acid have been described in the literature. It is an advantage of this invention that nucleic acid of a sample is easily electrostatically immobilized to a surface under a broad range of conditions. Therefore, an array of samples can be easily produced generally by just spotting (under electrostatic binding conditions) two or more samples containing nucleic acid at unique locations on a positively charged surface. Because the location of each sample is known, arrays of electrostatically immobilized nucleic acid can generally be used to simultaneously detect, identify or quantitate one or more target sequences in two or more samples of interest. Thus, an array of electrostatically immobilized nucleic acid may be useful in diagnostic applications or in screening compounds for leads which might exhibit therapeutic utility. An example of an array assay is Example 15 of this specification. Optionally, the non-nucleotide probe/target sequence hybrid is released from the matrix by adjustment of conditions outside the range required for electrostatic binding and thereby facilitates detection of the unbound non-nucleotide probe/target sequence hybrid, or just the detectable probe, as the means to detect, identify or quantitate the target sequence in the sample.

It is an advantage of this invention that the non-nucleotide probe is not necessary for the immobilization of the nucleic acid to the array matrix. Therefore, the non-nucleotide probe may be added to the one or more samples before or after they are electrostatically immobilized to the array matrix.

Arrays comprised of non-nucleotide probes/target sequence hybrids have the additional advantage that they are highly stable and should not be degraded by enzymes which degrade nucleic acid. Therefore, these arrays, or the samples which are to be applied to the array matrix, can be treated as described above in the Section entitled "Digestion/ Protection Assays" as a means to improve the assay performance by the degradation of sample contaminates. Regardless of whether the sample is treated with enzyme before or after it is applied to the array matrix, it is important that the non-nucleotide probe/target sequence be formed so that the target sequence is protected against degradation.

(v) Flow or Static Cytometric Assays

Flow and static cytometry are very useful for the analysis of whole cells as well as particles. Because the matrices of this invention can be beaded or particulate, this invention is particularly well suited for the static or flow cytometric analysis of particles containing nucleic acids electrostatically immobilized thereto. According to this invention, the nucleic acid is electrostatically immobilized to particles or beads. A non-nucleotide probe is used to detect a target sequence of interest present on the particles or beads and can be added before or after the nucleic acid is immobilized. Detection, identification or quantitation of the non-nucleotide probe/target sequence complex in the static or flow cytometer is used as the means to detect, identify or quantitate the target sequence in the sample of interest. Example 13 of this specification utilizes a static quantitation of fluorescence as the means to quantitate target sequence electrostatically immobilized to beads. Optionally, the non-nucleotide probe/target sequence hybrid is released from the matrix by adjustment of conditions outside the range required for electrostatic binding and thereby facilitates detection of the unbound non-nucleotide probe/target sequence hybrid, or just the detectable probe, as the means to detect, identify or quantitate the target sequence in the sample.

Exemplary Applications for Using the Invention

Because the methods, kits and compositions of this invention may be used in a probe-based hybridization assay, this invention will find utility in improving assays used to detect, identify of quantitate the presence or amount of an organism, virus, fungi or pathogen in a sample through the detection of target sequences associated with the organism or virus. (See: U.S. Pat. No. 5,641,631, entitled "Method for detecting, identifying and quantitating organisms and viruses" herein incorporated by reference). Similarly, this invention will also find utility in an assay used in the detection, identification or quantitation of one or more species of an organism in a sample (See U.S. Pat. No. 5,288,611, entitled "Method for detecting, identifying and quantitating organisms and viruses" herein incorporated by reference). This invention will also find utility in an assay used to determine the effect of antimicrobial agents on the growth of one or more microorganisms in a sample (See: U.S. Pat. No. 5,612,183, entitled "Method for determining the effect of antimicrobial agents on growth using ribosomal nucleic acid subunit subsequence specific probes" herein incorporated by reference). This invention will also find utility in an assay used to determine the presence or amount of a taxonomic group of organisms in a sample (See: U.S. Pat. No. 5,601, 984, entitled "Method for detecting the presence of amount of a taxonomic group of organisms using specific r-RNA subsequences as probes" herein incorporated by reference).

The methods, kits and compositions of this invention are particularly useful for the rapid, sensitive, reliable and versatile detection of target sequences which are particular to organisms which might be found in food, beverages, water, pharmaceutical products, personal care products, dairy products or environmental samples. The analysis of preferred beverages include soda, bottled water, fruit juice, beer, wine or liquor products. Consequently, the methods, kits and compositions of this invention will be particularly useful for the analysis of raw materials, equipment, products or processes used to manufacture or store food, beverages, water, pharmaceutical products, personal care products, dairy products or environmental samples.

Likewise, the methods, kits and compositions of this invention are particularly useful for the rapid, sensitive, reliable and versatile detection of target sequences which are particular to organisms which might be found in clinical environments. Consequently, the methods, kits and compositions of this invention will be particularly useful for the analysis of clinical specimens or equipment, fixtures or products used to treat humans or animals. For example, the assay may be used to detect a target sequence which is specific for a genetically-based disease or is specific for a predisposition to a genetically-based disease. Non-limiting examples of diseases include, β-Thalassemia, sickle cell anemia, Factor-V Leiden, cystic fibrosis and cancer related targets such as p53, p10, BRC-1 and BRC-2. The assay may also be used to detect a target sequence in aforensic technique such as prenatal screening, paternity testing, identity confirmation or crime investigation.

II. Preferred Embodiments of the Invention

Compositions

In one embodiment, this invention pertains to compositions suitable for detecting the presence of a target sequence in a sample. A preferred composition comprises a nucleic acid, having a target sequence, which is electrostatically bound to a matrix under suitable electrostatic binding conditions. The composition further comprises a non-nucleotide probe having a probing nucleobase sequence which is sequence specifically hybridized to at least a portion of the target sequence provided however that the non-nucleotide probe does not substantially bind to the matrix under suitable electrostatic binding conditions unless the target sequence is present on the matrix. Therefore, the electrostatic immobilization of the non-nucleotide probe/target sequence complex to matrix is primarily determined by the interaction of the nucleic acid with the matrix and not significantly dependent upon any interactions of the non-nucleotide probe and the matrix.

Such compositions are well suited for the detection of the presence of target sequences in samples since the nucleic acid components of the sample become concentrated on the matrix. Furthermore, the hybridized detectable non-nucleotide probe becomes concentrated on the matrix such that the limit of detection of the assay can be improved because the presence of the label is localized and thereby more easily detected as compared with when it is distributed in bulk fluid (See: Example 12).

Methods

In another embodiment, this invention pertains to methods for the detection, identification or quantitation of a target sequence in a sample containing nucleic acid. One exemplary method comprises contacting a sample with a matrix and at least one non-nucleotide probe wherein the nucleic acid in the sample will electrostatically bind to the matrix under suitable electrostatic binding conditions. Additionally, the non-nucleotide probe will hybridize, under suitable hybridization conditions, to at least a portion of the target sequence, if present in the sample. The method further comprises detecting, identifying or quantitating the non-nucleotide probe/target sequence hybrid as a means to detect, identify or quantitate the target sequence in the sample.

In still another embodiment, this invention pertains to multiplex methods for the detection, identification or quantitation of two or more target sequences of one or more nucleic acid molecules which may be present in the same sample. One exemplary method comprises contacting a sample with a matrix and two or more independently detectable non-nucleotide probes wherein the nucleic acid present in the sample will electrostatically bind to the matrix under suitable electrostatic binding conditions. Additionally, the two or more independently detectable non-nucleotide probes will hybridize, under suitable hybridization conditions, to at least a portion of the target sequences with which each probe is designed to hybridize if present in the nucleic acid of the sample. Consequently, if a particular target sequence is electrostatically immobilized to the matrix, the independently detectable non-nucleotide probe designed to hybridized to that particular target sequence will become concentrated on the matrix and be available for detection. Therefore, the method further comprises detecting, identifying or quantitating each unique independently detectable non-nucleotide probe/target sequence hybrid which is electrostatically bound to said matrix as a means to detect, identify or quantitate each unique target sequence sought to be detected in the sample and in the same assay. Optionally, the unique independently detectable non-nucleotide probe/target sequence hybrids is released from the matrix by adjustment of conditions outside the range required for electrostatic binding and thereby facilitates detection of the unbound non-nucleotide probe/target sequence hybrid, or just the detectable probe, as the means to detect, identify or quantitate the target sequence in the sample.

In still a further embodiment, this invention takes advantage of the stability of nucleic acid analog/nucleic acid complexes (See: Stanley et al.; U.S. Pat. No. 5,861,250) to thereby further improve assay performance and/or otherwise decrease the labor or complexity of sample preparation. One exemplary method comprises contacting the sample with at least one non-nucleotide probe wherein the non-nucleotide probe will hybridize, under suitable hybridization conditions, to at least a portion of the target sequence if present in the sample. The sample is also contacted with a matrix wherein the nucleic acid molecule will electrostatically bind to a matrix under suitable electrostatic binding conditions. Either before or after immobilization to the matrix, the sample containing the non-nucleotide probe/target sequence complex is contacted with one or more enzymes capable of degrading sample contaminants, including the nucleic acid molecule but not the non-nucleotide probe/target sequence complex. The method further comprises detecting, identifying or quantitating the non-nucleotide probe/target sequence hybrid as a means to detect, identify or quantitate the target sequence in the sample provided that the non-nucleotide probe/target sequence is first immobilized to the matrix. Optionally, the detectable non-nucleotide probe/target sequence hybrid is released from the matrix by adjustment of conditions outside the range required for electrostatic binding and thereby facilitates detection of the unbound non-nucleotide probe/target sequence hybrid, or just the detectable probe, as the means to detect, identify or quantitate the target sequence in the sample.

In yet another embodiment, this invention relates to a method for the detection, identification or quantitation of a target sequence of a nucleic acid molecule electrostatically immobilized at a location on an array wherein the array comprises nucleic acid molecules electrostatically bound at unique locations. One exemplary method comprises contacting the array with at least one non-nucleotide probe, wherein the non-nucleotide probe will hybridize, under suitable hybridization conditions, to at least a portion of the target sequence if present on the array. The non-nucleotide probe/target sequence complex electrostatically bound at a location on said array is then detected, identified or quantitated as the means to determine the presence, absence or amount of target sequence present at said array location. It is an advantage of the invention that one or more enzymes capable of degrading sample contaminants, including the nucleic acid target molecule but not the non-nucleotide probe/target sequence complex, can also be added before analysis of the array to thereby improve the performance of the array assay by degrading sample contaminants which might otherwise lead to false positive results. Optionally, the detectable non-nucleotide probe/target sequence hybrids can be released from the matrix by adjustment of conditions outside the range required for electrostatic binding and thereby facilitates detection of the unbound non-nucleotide probe/target sequence hybrid, or just the detectable probe, as the means to detect, identify or quantitate target sequence in the sample. If the non-nucleotide probes are independently detectable, the analysis of the matrix can proceed in a multiplex format.

In yet a further embodiment, this invention is directed to a method for the detection, identification or quantitation of a target sequence of a nucleic acid molecule which may be present in any of two or more samples of interest. The method comprises mixing each of the two or more samples of interest with at least one non-nucleotide probe, under suitable hybridization conditions. Next a matrix is contacted, under suitable electrostatic binding conditions, with at least a portion of each of the two or more samples to thereby electrostatically immobilize the nucleic acid components of each sample to the matrix, each at a unique location, and thereby create a matrix array of samples. The non-nucleotide probe/target sequence complex electrostatically bound at a location on said array is then detected, identified or quantitated as the means to determine the presence, absence or amount of target sequence present at said array location. It is an advantage of the invention that one or more enzymes capable of degrading sample contaminants, including the nucleic acid target molecule but not the non-nucleotide probe/target sequence complex, can also be added before analysis of the array to thereby improve the performance of the array assay by degrading sample contaminants which might otherwise lead to false positive results. Optionally, the detectable non-nucleotide probe/target sequence hybrids can be released from the matrix by adjustment of conditions outside the range required for electrostatic binding and thereby facilitates detection of the unbound non-nucleotide probe/target sequence hybrid, or just the detectable probe, as the means to detect, identify or quantitate target sequence in the sample. If the non-nucleotide probes are independently detectable, the analysis of the matrix can proceed in a multiplex format.

Kits

In yet another embodiment, this invention is directed to kits suitable for performing an assay, as described herein, which detects the presence, absence or number of target sequences in a sample. The kits of this invention comprise a matrix and one or more non-nucleotide probes and other reagents or compositions which are selected to perform an assay or otherwise simplify the performance of an assay used to detect, identify or quantitate a target sequence in a sample. Suitable non-nucleotide probes, matrices and methods have been previously described herein. Typically, the kit will comprise a non-nucleotide probe, a matrix and one or more reagents or buffers for fixing the electrostatic binding conditions and/or hybridization conditions.

One embodiment of a preferred kit will comprise at least two independently detectable non-nucleotide probes such that the presence absence or amount of each independently detectable moiety can be used to distinctly identify or quantitate each of at least two target sequences which may be present in a sample in the same assay (a multiplex assay). In a preferred embodiment, the kit will comprise two or more non-nucleotide "Beacon" probes. Preferably, the kit will be useful for performing a multiplex self-indicating assay such as a self-indicating PCR assay.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

This invention is now illustrated by the following examples which are not intended to be limiting in any way.

Example 1

Synthesis of DNA Oligonucleotides for Study

For this study, labeled and non-labeled DNA oligonucleotides suitable as probes or as nucleic acids comprising a target sequence were either synthesized using commercially available reagents and instrumentation or obtained from commercial vendors. All DNAs were obtained in purified form or purified using conventional methods. The sequences of the DNA oligonucleotides prepared are illustrated in Table 1, below. Methods and compositions for the synthesis and purification of synthetic DNAs are well known to those of ordinary skill in the art.

Example 2

Synthesis of N-α-(Fmoc)-N-ε-(NH$_2$)-L-Lysine-OH

To 20 mmol of N-α-(Fmoc)-N-ε-(t-boc)-L-lysine-OH was added 60 mL of 2/1 dichloromethane (DCM)/ trifluoroacetic acid (TFA). The solution was allowed to stir until the tert-butyloxycarbonyl (t-boc) group had completely been removed from the N-β-(Fmoc)-N-ε-(t-boc)-L-lysine-OH. The solution was then evaporated to dryness and the residue redissolved in 15 mL of DCM. An attempt was then made to precipitate the product by dropwise addition of the solution to 350 mL of ethyl ether. Because the product oiled out, the ethyl ether was decanted and the oil put under high vacuum to yield a white foam. The white foam was dissolved in 250 mL of water and the solution was neutralized to pH 4 by addition of saturated sodium phosphate (dibasic). A white solid formed and was collected by vacuum filtration. The product was dried in a vacuum oven at 35–40° C. overnight. Yield 17.6 mmol, 88%.

Example 3

Synthesis of N-α-(Fmoc)-N-ε-(dabcyl)-L-Lysine-OH

To 1 mmol of N-α-(Fmoc)-N-ε-(NH$_2$)-L-Lysine-OH (Example 2) was added 5 mL of N,N'-dimethylformarnide (DMF) and 1.1 mmol of TFA. This solution was allowed to stir until the amino acid had completely dissolved.

To 1.1 mmol of 4-((4-(dimethylamnino)phenyl)azo) benzoic acid, succinimidyl ester (Dabcyl-NHS; Molecular Probes, P/N D-9945) was added 4 mL of DMF and 5 mmol of diisopropylethylamine (DIEA). To this stirring solution was added, dropwise, the N-α-(Fmoc)-N-ε-(NH$_2$)-L-Lysine-OH solution prepared as described above. The reaction was allowed to stir overnight and was then worked up.

The solvent was vacuum evaporated and the residue partitioned in 50 mL of DCM and 50 mL of 100/ aqueous citric acid. The layers were separated and the organic layer washed with aqueous sodium bicarbonate and again with 10% aqueous citric acid. The organic layer was then dried with sodium sulfate, filtered and evaporated to an orange foam. The foam was crystallized from acetonitrile (ACN) and the crystals collected by vacuum filtration. Yield 0.52 mmol, 52%.

Example 4

Synthesis of N-β-(Fmoc)-N-ε-(dabcyl)-L-Lysine-PAL-Peg/PS Synthesis Support

The N-α-(Fmoc)-N-ε-(dabcyl)-L-Lysine-OH (Example 2) was used to prepare a synthesis support useful for the preparation of C-terminal dabcylated PNAs. The fluorenylmethoxycarbonyl (Fmoc) group of 0.824 g of commercially available Fmoc-PAL-Peg-PS synthesis support (PerSeptive Biosystems, Inc.; P/N GEN913384) was removed by treatment, in a flow through vessel, with 20% piperidine in DCM for 30 minutes. The support was then washed with DCM. Finally, the support was washed with DMF and dried with a flushing stream of argon.

A solution containing 0.302 g N-α-(Fmoc)-N-ε-(dabcyl)-L-Lysine-OH, 3.25 mL of DMF, 0.173g [O-(7-azabenzotriaol-1-yl)-1,1,3,3-tetramethyluronium hexafluorophosphate (HATU), 0.101 mL DIEA and 0.068 mL 2,6-lutidine was prepared by sequential combination of the reagents. This solution was then added to the washed synthesis support and allowed to react for 2 hours. The solution was then flushed through the vessel with a stream of argon and the support washed sequentially with DMF, DCM and DMF. The resin was then dried with a stream of argon.

The support was the treated with 5 mL of standard commercially available PNA capping reagent (PerSeptive Biosystems, Inc., P/N GEN063102). The capping reagent was then flushed from the vessel and the support was washed with DMF and DCM. The support was then dried with a stream of argon. Finally, the synthesis support was dried under high vacuum.

Final loading of the support was determined by analysis of Fmoc loading of three samples of approximately 6–8 mg. Analysis determined the loading to be approximately 0.145 mmol/g.

This synthesis support was packed into an empty PNA synthesis column, as needed, and used to prepare PNA oligomers having a C-terminal dabcyl quenching moiety attached to the PNA oligomer through the ε-amino group of the C-terminal L-lysine amino acid.

Example 5

Synthesis of PNA

PNAs were synthesized using commercially available reagents and instrumentation obtained from PerSeptive Biosystems, Inc. Double couplings were often performed to insure that the crude product was of acceptable purity. Purity of the final PNAs was determined by standard reversed-phase chromatographic methods and the identity of the PNA confirmed by comparison of theoretical calculated masses with results of mass analysis using a MALDI-TOF mass spectrometer.

PNAs possessing a C-terminal dabcyl moiety were prepared by performing the synthesis using the dabcyl-lysine modified synthesis support prepared as described in Example 4. PNAs possessing an N-terminal fluorescein moiety were treated with the appropriate labeling reagents and linkers (as required) prior to cleavage from the synthesis support (See: Example 6). Several methods are available for labeling a PNA oligomer with fluorescein but Applicants preferred method is described in Example 6. PNAs comprising a Cy3 label (Amersham) were cleaved from the synthesis support and HPLC purified using conventional methods prior to Cy3 labeling as described in Example 7.

Example 6

Preferred Procedure for Labeling of Support Bound PNA with 5(6)carboxyfluorescein After proper reaction with linkers and removal of the terminal amine protecting group, the resin was treated with 250 μL of a solution containing 0.5 M 5(6) carboxyfluorescein, 0.5 M N,N'-diisopropylcarbodiimide, 0.5M 1-hydroxy-7-azabenzotriazole (HOAt) in DMF (See: Weber et al., *Bioorganic & Medicinal Chemistry Letters,* 8: 597–600 (1998). After treatment the synthesis support was washed and dried under high vacuum. The PNA oligomer was then cleaved, deprotected and purified.

Example 7

General Procedure for Cy3 Labeling of PNAs

The purified amine containing PNA was dissolved in 1/1 DMF/water at a concentration of approximately 0.05 OD/μL to prepare a stock PNA solution. From the stock, approximately 30 nmole of PNA was added to a tube. To this tube was then added 125 μL 0.1 M HEPES (pH 8.5), and enough 1/1 DMF/water to bring the total volume to 250 μL. This solution was thoroughly mixed. To a prepackaged tube of Cy3 dye (Amersham), was added the entire 250 μL solution prepared as described above. The tube was well mixed and then allowed to react for 1 hour at ambient temperature.

After reaction, the solvent was removed by evaporation in a speed-vac. The pellet was then dissolved in 400 μL of a solution containing 3:11% aqueous TFA/ACN. Optionally the solution was then transferred to a 5000 MW Ultrafree (Millipore, P/N UFC3LCC25) or a 3000 MW (Amicon, P/N 42404) and filtered to remove excess dye. The recovered product was then repurified using conventional reversed phase chromatographic methods.

General Discussion of Examples 8 to 12

The following Examples were performed to examine whether the presence of target nucleic acids which had been electrostatically bound to polyethylene imine (PEI) derivatized beads could be specifically detected using labeled PNA probes wherein the labeled (neutral) PNA would not become immobilized to the beads in the absence of target nucleic acid but would hybridize, and therefore become immobilized to the beads, if the target nucleic acid was present. These experiments demonstrate an application which is uniquely suited to PNA probes since they possess a neutral backbone but nevertheless hybridize to nucleic acids with sequence specificity.

Aided by the discussion and examples described herein, those of skill in the art will appreciate that positively charged matrices other than those coated with PEI are suitable for the practice of the invention described herein. Similarly, those of skill in the art will appreciate that all kinds of matrices or supports, other than beads, are suitable for the practice of this invention. Finally, those of skill in the art will also appreciate that the non-nucleotide probes suitable for the practice of this invention include present (e.g. PNA) and future constructs which sequence specifically interact with nucleic acid and which are either neutral or positively charged under conditions wherein a nucleic acid will electrostatically bind to a charged matrix.

TABLE 2

PNA Probes

| Description | PNA Sequence |
|---|---|
| WT-15Flu | Flu-OO-ACG-CCA-CCA-GCT-CCA-$NH_2$ |
| MU-15Flu | Flu-OO-ACG-CCA-CAA-GCT-CCA-$NH_2$ |
| MU-15Blocker | $H_2$N-OO-ACG-CCA-CAA-GCT-CCA-$NH_2$ |
| BK.RAS-Cy3 | Cy3-O-ACG-CCA-CCA-GCT-CCA-K(dabcyl)-$NH_2$ |
| UQ-Cy3 | Ce-OO-TGA-TTG-CGA-ATG-K(Cy3)-$NH_2$ |
| RASWT-Cy3 | Cy3-OOE-ACG-CCA-CCA-GCT-CCA-E-$NH_2$ |
| BioP-15 | Ac-OE-TTA-TAC-TGC-TAG-CCT-EO-K(Bio)-$NH_2$ |

All PNA sequences are written from the amine to the carboxyl terminus. Abbreviations are:Ac=acetyl; Flu=5(6)-

TABLE 1

Oligodeoxynucleotide Probes and Constructs

| Description | Oligodeoxynucleotide Sequence | Seq. ID No. |
|---|---|---|
| KRASWT(24) | Biotin-GTG-GTA-GTT-GGA-GCT-GGT-GGC-GTA-OH | 1 |
| KRASMU(24) | Biotin-GTG-GTA-GTT-GGA-GCT-TGT-GGC-GTA-OH | 2 |
| KRASMU(31) | Biotin-GTG-GTA-GTT-GGA-GCT-TGT-GGC-GTA-GGC-AAG-A-OH | 3 |
| WT-15Flu | Flu-ACG-CCA-CCA-GCT-CCA-OH | 4 |
| MU-15Flu | Flu-ACG-CCA-CAA-GCT-CCA-OH | 5 |
| pBR322 5' primer | HO-GCT-TGT-TTC-GGC-GTG-GGT-AT-OH | 6 |
| pBR322 3' primer | HO-TAG-GTT-GAG-GCC-GTT-GAG-CA-OH | 7 |
| KRAS 5' primer | HO-ATG-ACT-GAA-TAT-AAA-CTT-GT-OH | 8 |
| KRAS 3' primer | HO-CTC-TAT-TGT-TGG-ATC-ATA-TT-OH | 9 |
| CompDNA | HO-TCA-CTA-GTC-CCT-TCA-AGG-CTA-GCA-GTA-TAA-TGG-GTT-CTA-GGT-AAA-CGT-TCC-ACC-GTT-ACT-OH | 10 |
| NonCompDNA | HO-AGT-AAC-GGT-GGA-ACG-TTT-ACC-TAG-AAC-CCA-TTA-TAC-TGC-TAG-CCT-TGA-AGG-GAC-TAG-TGA-OH | 11 |

All oligodeoxynucleotides are illustrated from the 5' to the 3'. Stock solutions of the oligodeoxynucleotides were generally prepared by dissolving the dry powder in TE Buffer (TE Buffer: 10 mM TRIS pH 8.3, 1 mM EDTA).

Materials:

| PEI-Silica beads (gel) | Amicon | P/N | PAE-300-15 |
| HP-Sepharose Q beads | Pharmacia Biotech | P/N | 17-1014-03 |

Commercially available PEI derivatized beads were chosen for these experiments since they were readily available as well characterized commercial anion exchange chromatography packing materials having a high density of positively charged functional groups per unit area at neutral pH (pH of 7). Because they possessed a high density of positively charged functional groups at neutral pH, they possessed a favorable binding capacity for oligonucleotides which are negatively charged (because each phosphodiester comprises a single negative charge the charge of each nucleic acid is length dependent) at neutral pH.

PEI-Silica and PEI-Sepharose beads were determined to be essentially interchangeable in all experiments performed. However, the PEI-Silica beads were found to have an intrinsic (native) fluorescence when illuminated on the UV transilluminator, and for that reason may be less suitable in some applications.

carboxyfluorescein; dabcyl=4-((4-(dimethylamino)phenyl)azo)benzoic acid; Bio=biotin; O=8-amino-3,6-dioxaoctanoic acid; K=the amino acid L-Lysine; E=the solubility enhancer "4" as represented in Gildea et al., Tett. Lett. 39 (1998) 7255–7258; Ce=the group obtained by capping the PNA with the charged moiety "7" as represented in Gildea et al., Tett. Lett. 39 (1998) 7255–7258 and Cy3=the cyanine 3 dye from Amersham. Stock solutions of PNAs are generally prepared by dissolving the purified probe in a solution containing 1/1 N,N'-dimethylformarnide (DMF)/water at a concentration of approximately 0.05 OD (260 nm) per $\mu$L.

DNA Plasmid Templates

The plasmids, pKRASMU(31) and pKRASWT, were used as templates in PCR amplification reactions and were generated by cloning a PCR amplicon from human DNA into the pCR2.1 plasmid (Invitrogen). The mutant human DNA was prepared from a cell line, Calu-1, which contains a point mutation at base 129 of the K-ras gene. The wild type human DNA was prepared from a cell line, NCI, which contains two copies of the wild type K-ras gene. Clones were screened by restriction fragment analysis and sequence analysis. Large preparations of the plasmid were generated and quantitated using standard techniques. The amplified region flanks the K-ras mutation and was 111 bp in length.

```
dsDNA Template (amplified region only)
     <- 3' primer hyb. site ->

3' GAGATAACAACCTAGTATAAGCAGGTGTTTTACTAAGACTTA...

5' CTCTATTGTTGGATCATATTCGTCCACAAAATGATTCTGAAT...

<- Linear Beacon Hyb. site->

...ATCGACTTAGCAGTTCCGTGAGAACGGATGCGGTG(G/T)TCGAGGTT...

...TAGCTGTATCGTCAAGGCACTCTTGCCTACGCCAC(C/A)AGCTCCAA...

...GATGGTGTTCAAATATAAGTCAGTA 5' Seq. ID No. 12 (wt), 13
 (mu)

...CTACCACAAGTTTATATTCAGTCAT 3' Seq. ID No. 14, (wt), 15
 (mu)

<- 5' primer hyb. site ->
```

The position and sequence of the point mutation of the amplicons is illustrated in parenthesis. Plasmid pBR322 was obtained from New England BioLabs; P/N 300-3S.

TABLE 3

Salt Buffers:

| Buffer ID | Buffer Components: |
|---|---|
| A | 0 mM NaCl, 10 mM TRIS-Cl pH 8.0, 1 mM EDTA, 0.1% Tween-20. |
| B | 100 mM NaCl, 10 mM TRIS-Cl pH 8.0, 1 mM EDTA, 0.1% Tween-20. |
| C | 200 mM NaCl, 10 mM TRIS-Cl pH 8.0, 1 mM EDTA, 0.1% Tween-20. |
| D | 300 mM NaCl, 10 mM TRIS-Cl pH 8.0, 1 mM EDTA, 0.1% Tween-20. |
| E | 400 mM NaCl, 10 mM TRIS-Cl pH 8.0, 1 mM EDTA, 0.1% Tween-20. |
| F | 500 mM NaCl, 10 mM TRIS-Cl pH 8.0, 1 mM EDTA, 0.1% Tween-20. |

| Electrophoresis Supplies: | |
|---|---|
| 10–20% polyacrylamide gel: | ESA, catalog #80-0015 |
| 10X Gel Buffer: | ESA, catalog #80-0132 |
| 4X loading dye: | 50% glycerol, 0.1M Bromphenol Blue, 0.01 M Xylene Cyanol, 4X ESA Gel Buffer (diluted from ESA# 80-0132) |

Example 8

General Properties of Polyethylene imine (PEI) Beads

Polyethylene imine (PEI) beads were examined to determine physical characteristics such as particle size and shape as well as chemical properties such as binding capacity of nucleic acid. Particle size and concentration of beads suspended per unit of volume were determined using a hemacytometer (Hausser Scientific; Horsham, Pa.; Model # 3900).

Using the hemacytometer, the Sepharose beads were found to generally be spherical in shape and have a diameter in the range of approximately 20 to 50 µm with an estimated average diameter of 30 µm. The concentration of the suspended Sepharose beads was estimated to be approximately 50,000 beads/µL, after being washed (per manufactures instructions) and redissolved in deionized water.

Using the hemacytometer, the silica beads were found to also generally be spherical in shape and have a diameter in the range of approximately 5 to 15 µm with an estimated average diameter of approximately 10 µm. The concentration of the suspended silica beads was estimated to be approximately 150,000–200,000 beads/µL, after being washed (per manufactures instructions) and redissolved in deionized water.

The capacity of the silica and Sepharose beads to bind nucleic acid was examined in 100 mM TRIS-HCl pH 7.5. The capacity of the Sepharose beads was approximated to be about 0.75 $OD_{260}$ of nucleic acid per µL of beads, or approximately 1.1 E-5 $OD_{260}$ of nucleic acid per bead. The capacity of the silica beads was approximated by applicant to be about 0.4 $OD_{260}$ of nucleic acid per µL of beads, or approximately 0.8 E-6 $OD_{b\ 260}$ of nucleic acid per bead. For all experiments conducted, these binding capacities were high enough such that all the nucleic acid of the sample was expected to be electrostatically bound to the support given the amount of matrix present in the assay and the electrostatic binding conditions used.

Example 9

Preliminary Studies on [Salt] and pH

As discussed above, the silica and Sepharose beads are commercially available anion exchange chromatography media. As anion exchange chromatography often utilizes a salt gradient or pH gradient to elute materials which are electrostatically bound thereto, the effect of modulation in salt concentration and pH variation on the binding of PNA and/or DNA probes to Sepharose beads was studied to determine suitable electrostatic binding conditions for subsequent experimentation.

i. [Salt]

To individual tubes containing 5 µL of Sepharose beads and 94 µL of one of each of six salt solutions (Salt Buffers A–F, See: Table 3, above) was added 5 pmole (in 1 µL of an appropriate solvent) of either DNA WT-15Flu (Table 1) or PNA WT-15Flu (Table 2) probe. The tubes were vortexed, briefly centrifuged and then examined under UV light to determine whether the fluorescently labeled probes were still predominately in solution or whether they had adsorbed onto the surface of the beads.

The PNA probe (PNA WT-15Flu, Table 2) was found to be predominately adsorbed to the beads when in Salt Buffers A and B, but predominately in solution when all the buffers of higher salt concentration were used. This results indicated that the fluorescein labeled PNA probe would only bind to the beads at low ionic strength (approximately 200 mM NaCl or below).

By comparison, the fluorescein labeled DNA probe, (DNA WT-15Flu, Table 1) of identical subunit length and nucleobase sequence, was found to be substantially adsorbed to the beads except when Buffer F was present. In Buffer F, some of the probe was observed in the solution. This data indicated that at least 500 mM NaCl was required to disrupt the electrostatic interactions of the 15-mer DNA probe and the PEI on the surface to thereby free the probe from the matrix.

Though the difference of 200 mM NaCl to release the PNA 15mer as compared with 500 mM for release of the DNA 15 mer was significant enough to be useful for the practice of may embodiments of this invention, the requirement for 200 mM NaCl to release PNA probe from the PEI surface was surprising and therefore prompted subsequent examination. Upon further analysis, the presence of the fluorescein label (5(6)-carboxyfluorescein), which possess two negative charges at neutral pH, was determined to be the primary reason for the strong electrostatic interactions between the PNA probe and the PEI derivatized beads.

By way of example, a Cy3-labeled PNA 15-mer (UQ-Cy3, Table 2) which comprised a positively charged capping group was examined in the Salt Buffers listed in Table 3, above. It was found that the Cy3 labeled PNA did not bind to the beads even in Salt Buffer A. Furthermore, free fluorescein was found to be substantially adsorbed to the beads in Salt Buffer A, whereas; the Cy3 dye did not. Finally, it was determined that 1 $\mu$L of the Sepharose beads could adsorb as much as 5 pmole of 5(6)-carboxyfluorescein when in Salt Buffer A. Consequently, this data suggests that it was the fluorescein label and not the PNA portion of the oligomer which exhibited the strong interaction with the PEI derivatized beads in Salt Buffers A and B. Thus, it is believed that native PNA does not substantially electrostatically bind to the PEI even under low salt conditions (e.g. Salt Buffer A). This is consistent with expectations since PNA is neutral and should therefore not be expected to electrostatically bind to the PEI derivatized beads.

ii. pH Effects

Because the net charge on the PNA backbone should not change dramatically at pH in the range of 5–10, the effect of modulation in pH upon the binding of PNA to PEI derivatized beads was not examined. However, the pH dependency of DNA binding to PEI derivatized silica beads was examined to determine working parameters for subsequent experimentation. The results of experiments can be summarized as follows: At pH 7.3, the WT-15Flu DNA probe stayed bound to the silica beads up to 0.8 M NaCl, whereas; at pH 8.3, the same probe did not bind to the beads at NaCl concentrations in excess of 0.1 M.

These results can be correlated with the number of expected positively charged functional groups of the PEI support. The higher capacity at pH 7.3 indicates that the support is more highly charged (higher charge density) under these conditions. However, at pH 8.3, the pH of the solution is approaching the pK of the secondary amine of the PEI and therefore the support begins to become neutralized (fewer positive charges per unit area). With fewer positive charges, each bead has a lower affinity for the negatively charged oligodeoxynucleotides. Therefore, less salt is required to disrupt the electrostatic interactions and thereby release the DNA into the solution.

Example 10

Preliminary Examination of Hybrid Formation of Immobilized DNA

A study was conducted to determine whether hybridization of the PNA probes would occur with nucleic acid electrostatically immobilized to the surface of the Sepharose beads. For this experiment, 1 pmole of the MU-15Flu PNA probe was allowed to hybridize to 0.5 pmole of the KRASMU(31) DNA target which was either free in solution or electrostatically bound to Sepharose beads (1 $\mu$L of a 1:10 dilution of bead stock in Buffer E). "PNA only" (probe) and "DNA only" (target sequence) controls were also examined. The hybridization reactions were allowed to proceed for approximately 2 minutes, after which, 1 $\mu$L of the 1:10 dilution of bead stock was added to the sample which did not initially contain Sepharose beads.

The hybridization reaction contents were then suctioned into individual capillary pipettes from which the liquid was wicked thereby leaving behind the beads and any bound and fluorescently labeled PNA/DNA hybrids. The "PNA only" and "DNA only" controls were found to be non-fluorescent under UV light. However, by visual inspection, both of the PNA/DNA hybridization reactions were equally fluorescent. Consequently, this data indicates that the PNA can hybridize with roughly equivalent efficiency to both the DNA electrostatically immobilized to a Sepharose beads as well as it can hybridize to the DNA free in solution.

Example 11

Efficiency of Electrostatic Capture and Release

A study was performed to determine the efficiency of the electrostatic capture and release of nucleic acid at very low nucleic acid concentrations. Because the amount of nucleic acid was extremely small, the polymerase chain reaction (PCR) was used to quantify the captured and recovered nucleic acid. The plasmid pBR322 (New England Biolabs; PN/ P/N 300-3S) was used at concentrations ranging from 5 E+11 to 5 E+5 molecules (approximately 1 attomole) per microliter.

Plasmid DNA was captured over a period of 5 minutes using 1 SL of PEI-Silica beads in 20 $\mu$L of 100 mM TRISHCl, pH 7.6. After capture, the samples were pelleted by centrifugation, the supernatants were removed, and the beads were washed with 1000 $\mu$L of 100 mM TRIS-HCl pH 7.6 to removed non-specifically bound material. The plasmid DNA was then released from the beads by treatment with 10 $\mu$L of a high salt buffer containing 2 M NaCl and 100 mM TRIS-HCl pH 7.6. One microliter of each bead eluate was then added to 99 $\mu$L of 100 mM TRIS-HCl pH 7.6 to dilute the NaCl concentration down to a level acceptable for PCR. Two microliters of each diluted sample was then added to a 50 $\mu$L PCR reaction.

In addition, each PCR reaction also contained, 5 pmole of 5' pBR322 primer, 5 pmole of 3' pBR322 primer, 3 mM $MgCl_2$, 250 $\mu$M NTPs, 2.0 units AmpliTaq DNA polymerase, 50 mM KCl, and 10 mM Tris-HCl pH 8.3 (PCR reagents including 10×buffer, magnesium chloride solution, AmpliTaq DNA polymerase, and nucleotide triphosphates were obtained from Perkin-Elmer, Foster City, Calif.). Reactions were performed in mini-eppendorf tubes using a Perkin-Elmer 2400 thermocycler. The PCR protocol involved a 20 second warm up to 95° C. (1st round only), followed by denaturing at 95° C. for 20 seconds, annealing at 56° C. for 20 seconds, and extension at 74° C. for 20 seconds. The denaturation-annealing-extension cycle was repeated for 30 cycles, followed by a final extension step at 74° C. for 5 minutes.

All of the samples were run on a polyacrylamide gel after PCR, and all contained detectable levels of the correct sized amplicon, though the most dilute sample (5 E+5 input molecules) was barely detectable. The amount of DNA in the PCR reaction was actually 500 fold less (1 E+3 molecules) due the dilution necessary to remove salt, as described above. In a control experiment run at the same time, 1 E+3 molecules was the limit of detection of pBR322 by 30 cycles of PCR. These results suggest that at 5 E+5 molecules of input template, the majority of the plasmid DNA initially added to the matrix was captured and released.

Example 12

Self-Indicating PCR Assays

Self-indicating and closed-tube assays are becoming increasingly popular for their ability to streamline, simplify and potentially automate routine nucleic acid analysis assays. Also, closed-tube assays prevent carry-over contamination between samples which is a major source of false positive results in nucleic acid diagnostics. Since the concentration of detectable moieties is an advantage associated with the electrostatic binding of nucleic acids to matrices, it was envisioned that it might be possible to create a self-indicating PCR assay wherein the fluorescence of the matrix enclosed in the reaction, at the time the reaction components are mixed, could be used to determine the result of a PCR amplification by mere visual or instrument monitoring of the tube during and/or after PCR was completed.

Point mutation analysis is another important objective of a nucleic acid diagnostic test since accurate determination of a specific point mutation of genetic material in a sample is often a decisive factor in the proper identification of genetic disorders and other disease states. As discussed in the specification, blocker probes can be used to improve single point mutation analysis of a probe-based assay beyond the limits which are possible by the precise optimization or control of stringency. Thus, it was envisioned that the use of PNA Blocker probes in conjunction with Linear Beacons would facilitate the development of a self-indicating probe based assay capable of point mutation discrimination which would generate a result which could be interpreted by visual inspection or by instrument analysis during and/or after the PCR was completed.

For Examples A and B, asymmetric PCR was utilized because asymmetric PCR yields a significant excess of single stranded nucleic acid. Since it is possible to choose which of the strands of the amplicon are preferentially amplified by judicious adjustment of the ratio of 5' and 3' primers, it was possible to design the assay so that the target sequence to which the non-nucleotide probe hybridizes was contained within the over produced single stranded nucleic acid of the asymmetric PCR assay.

For Examples A and B, a Linear Beacon was chosen as the non-nucleotide probe since Linear Beacons are inherently non-fluorescent (or very slightly fluorescent) until hybridized to the target sequence. This approach was advantageous since the reaction cocktail containing the Linear Beacon would remain relatively non-fluorescent throughout the assay and in theory, only the beads would become fluorescent provided the target sequence was generated and electrostatically bound to the matrix (beads). Thus, the Linear Beacon (BK.RAS-Cy3; See Table 2, above) was designed to hybridize to the over produced strand of a region of dsDNA (See: illustration on p. 28) sought to be amplified and was added to the PCR cocktail before thermocycling. The Linear PNA Beacon was labeled with Cy3 since prior experiments had demonstrated that the negatively charged fluorescein label exhibited an affinity for the PEI coated beads at salt concentrations of less than 200 mM.

Though Linear Beacons may hybridize to the target sequence during thermocycling, significant inhibition of the amplification process was not observed. Consequently, the PCR amplification was successfully monitored using the detectable fluorescent signal of the Linear Beacon which was generated on the surface of the beads in response to the activity of the PCR reaction. The data presented conclusively demonstrates the feasibility of using Linear Beacons for the detection or point mutation analysis of nucleic acid electrostatically bound to a matrix which has been generated by amplification in a closed tube assay. As evidenced by FIGS. 1 and 3, the result can be determined by mere visual inspection of the final assay sample still in the tube. Since fluorescence is visible to the naked eye, a sensitive instrument, such as a Prism 7700, would be suitable for real-time or end-point automated sample analysis. The figures further demonstrate that concentration of the samples on the matrix makes it possible to improve the limits of detection of the assay since the signal intensity on the beads is far more intense than the signal generated by the bulk fluid when the Linear Beacon is free in solution.

A. Asymmetric PCR with Linear Beacons

PCR Materials & Methods

This experiment comprised five individual PCR reactions. Variable factors examined within the set of five reactions included the presence or absence of PEI derivatized Sepharose beads (approximately 25,000 PEI-Sepharose beads), the presence or absence of plasmid template (pKRASWT at 20 fmole per 50 μL reaction (0.4 nM)) and the presence or absence of thermocycling (TMC). Table 4, below, summarizes the composition of various tubes with respect to these variable factors. In addition, each PCR reaction contained 1.5 μL of 100% glycerol, 0.5 μL of water (control) or Sepharose beads, 45 pmole of KRAS 5' primer, 5 pmole of the KRAS 3' primers, 3 mM $MgCl_2$, 250 μM NTPs, 2.0 units AmpliTaq DNA polymerase, 50 mM KCl, 10 mM TRIS-Cl pH 8.3, and 50 pmole BK.RAS-Cy3 non-nucleotide probe (Linear Beacon) in a total volume of 50 μL. During preparation and prior to PCR, the tubes were carefully handled to avoid mixing of components.

The PCR protocol involved a 20 second warm up to 95° C. (1st round only), followed by denaturing at 95° C. for 5 seconds, annealing at 55° C. for 30 seconds, and extension at 74° C. for 30 seconds. The denaturation-annealing-extension cycle was repeated for 50 cycles, followed by a final extension step at 74° C. for 5 minutes.

After thermocycling, the tubes were placed on a transilluminator and the fluorescence examined by eye. Thereafter, the tubes were vortexed and then centrifuged for 2 minutes to concentrate the beads at the tube bottom. No significant difference was observed whether or not the tubes were vortexed and centrifuged before viewing. This indicated that the glycerol did not affect the end point result.

Notes

1. The glycerol was added to temporarily shield the beads from the reaction components in the early stages of PCR so that the process would not be substantially inhibited by electrostatic binding of the primers to the matrix (beads) during the critical early thermocycles. Subsequent investigations have demonstrated that the presence of a temporary shield is not essential to achieve an accurate result but is nevertheless preferred.

TABLE 4

| Tube # | PEI-Beads | Template | TMC |
|---|---|---|---|
| | Variable Factors | | |
| 1 | — | pKRASWT | no |
| 2 | — | — | yes |
| 3 | — | pKRASWT | yes |
| 4 | Sepharose | — | yes |
| 5 | Sepharose | pKRASWT | yes |

Post PCR Workup/Analysis

Figure 1B:
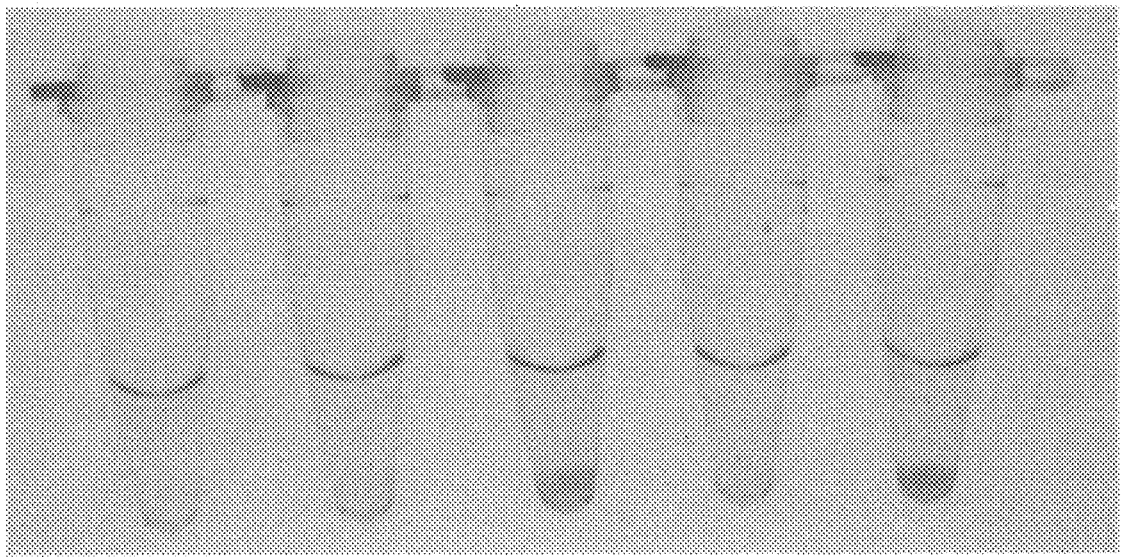

After PCR, tubes 1–5 were placed on a transilluminator to visualize fluorescence and then photographed. FIG. 1A is a negative of the scanned image of the photograph taken of the five mini-eppendorf tubes immediately after PCR (tubes are labeled 1–5). After the photograph was taken, 0.5 μL of the PEI-Sepharose bead stock was added to tubes 1–3. The five tubes were then vortexed, centrifuged and again placed on the transilluminator and again photographed. FIG. 1B is a negative of the scanned image of the second photograph of the five mini-eppendorf tubes.

After re-photographing the tubes, the supernatants were decanted and the beads were washed with 100 μL of a solution containing 50 mM NaCl and 100 mM TRIS-HCl pH 7.6. Washing involved adding the wash buffer, vortexing briefly, centrifuging and then decanting. The electrostatically bound nucleic acids were then released from the beads for analysis by vortexing in a solution containing 10 μL of 0.05% ammonium hydroxide and 2.0 M NaCl. Supernatants were removed and transferred to a microwell plate where they were neutralized with 1 μL 0.1 N hydrochloric acid. To each well was added 4 μL of 4×loading dye. Finally, 15 μL of each sample was then run on a 10–20% gradient gel to confirm nucleic acid amplification and identify product size.

Figure 2A:
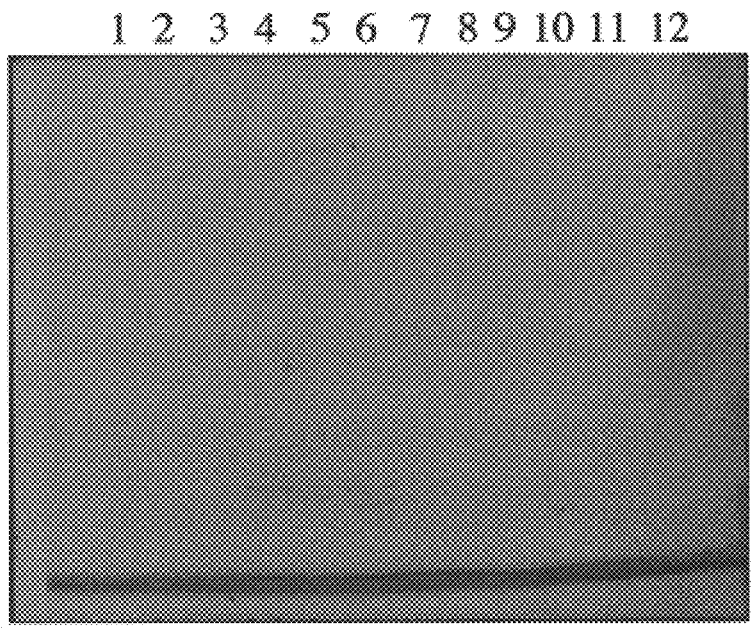
FIGS. 2A and 2B are computer generated negatives of the image of a photograph of the same polyacrylamide gel used to analyze the content of the tubes shown in FIGS. 1A and 1B, before (FIG. 2A) and after (FIG. 2B) ethidium bromide staining.
Figure 2B:
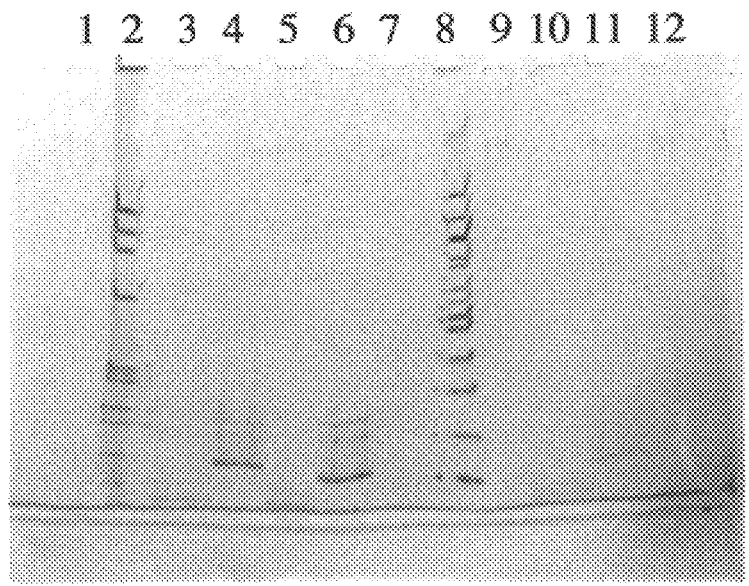

FIGS. 2A and 2B are the negative of images of photographs of the same 10–20% gradient polyacrylamide gel illuminated on a UV transilluminator which were taken before and after ethidium bromide staining, respectively.

Results

Tube Images/photographs

With regard to analysis of the images of the photographs, please note that although black and white photographs were taken, visual inspection of the tubes was consistent with the dark to light contrast seen in the images except that the Cy3 dye appeared as orange to the eye under the transilluminator. Furthermore, the negative (generated electronically) of the scanned image is shown since it is believed that the contrasts of the negative image are superior for illustration and will be more accurately reproduced by photocopying.

With reference to FIG. 1A, the results are as expected. Tube 1 was a control which was not exposed to thermocycling and therefore little or no fluorescence was observed (the tube contents appear clear in contrast to the background). Likewise, tubes 2 and 4 contained no template and therefore little or no fluorescence was observed in solution (tube 2) or on the beads (tube 4) since no amplification should have occurred. Tube 3, however, was fluorescent as expected since amplification of the template should have produced the 111 bp amplicon to which the Linear Beacon hybridized to generate detectable signal. Nevertheless, since no Sepharose was present, the solution was visibly orange as compared with tubes 1, 2 and 4. Likewise, tube 5 contained highly fluorescent (orange by eye; dark in the negative of the image) beads as expected since amplification of the template should have produced the 111 bp amplicon (electrostatically bound to the bead matrix) to which the Linear Beacon hybridized to generate a detectable signal.

With reference to FIG. 1B, the results are also as expected. Specifically, the addition of the Sepharose beads to tubes 1–3 only affected the fluorescence of tube 3. In particular, the orange fluorescence which was observed to be in solution prior to the addition of the Sepharose beads, was concentrated on the bead surface (dark in the negative of the image) after bead addition. Furthermore, the intensity of the fluorescence of tube 3, which could be determined visually, was comparable to the fluorescence intensity of the beads in tube 5. Thus, there appears to be no difference in the result whether or not the matrix is added before or after the PCR reaction is performed.

In summary, the data presented in FIGS. 1A and 1B indicate that it is possible to perform self-indicating amplification assays wherein signal of a probe can be concentrated on a matrix to which an amplified target nucleic acid is electrostatically immobilized.

Gel Photographs/images

Analysis of the PCR reactions by gel was performed to determine the presence and size of amplicons to thereby confirm that the visual analysis of the tubes correlated with expected products of PCR amplification.

With reference to FIGS. 2A and 2B, the wells of the gel are at the top of the photographs. Aliquots of each tube were added near the top of the gel and electrophoretically directed towards the bottom of the gel. Lanes 2 and 8 contain two different double stranded DNA size markers; lane 2 is ØX174/HaeIII (New England BioLabs #303-1S) and lane 8 is a 100 bp ladder (New England BioLabs #323-1L). Band sizes are indicated in FIG. 2B. Lanes 3–6 contain samples of released nucleic acid isolated from the beads in tubes 2 through 5 respectively and lane 7 contains material released from the beads in tube 1.

With reference to FIG. 2A, the presence of inherently fluorescent bands can be seen in lanes 4 and 6 (from tubes 3 and 5 respectively) toward the bottom of the image. The fluorescent bands can be attributed to the presence of the Linear Beacon still hybridized to the nucleic acid amplicon even after it has migrated into the gel. This result is consistent with amplification in tubes 3 and 5 as indicated by the visual analysis of the tubes. By comparison, there are no visible fluorescent bands in any of lanes 3, 5, and 7. This result is consistent with the lack of amplification as indicated by visual analysis of the tubes.

With reference to FIG. 2B, all nucleic acid is fluorescent because it is stained with ethidium bromide. Therefore, the size markers in lanes 2 and 8 are now visible. Strong fluorescent bands having a size consistent with the expected 111 bp product are visible in lanes 4 and 6 but are absent in lanes 3, 5 and 7. This data confirms production of the intended amplicon only in tubes 3 and 5 and further confirms that the nucleic acid was recovered from material originally electrostatically bound to the Sepharose beads.

In summary, the data presented in FIGS. 1A and 1B, when considered with the data presented in FIGS. 2A and 2B, conclusively demonstrates that it is possible to perform self-indicating amplification assays wherein signal of a probe can be concentrated on a matrix to which an amplified target nucleic acid is electrostatically immobilized.

B. Single Point Mutation Analysis

This experiment was used to examine whether or not it was possible to achieve point mutation discrimination in the self-indicating probe-based assay. Unless otherwise stated, this experiment was conducted essentially as described in part A, above, except that an unlabeled PNA oligomer (blocker probe) was added to achieve single point mutation discrimination. Since control reactions not containing the blocker probe were performed, a comparison of the results obtained in the presence and absence of blocker probe clearly demonstrates the remarkable improvement in target sequence identification resulting from the presence of the blocker probe.

TABLE 5

Variable Factors

| Tube # | PEI-Beads | Template | Blocker Probe |
|---|---|---|---|
| 1 | — | — | — |
| 2 | — | pKRASWT | — |
| 3 | — | pKRASMU(31) | — |
| 4 | Sepharose | — | — |
| 5 | Sepharose | pKRASWT | — |
| 6 | Sepharose | pKRASMU(31) | — |
| 7 | Sepharose | — | MU-15Blocker |
| 8 | Sepharose | pKRASWT | MU-15Blocker |
| 9 | Sepharose | pKRASMU(31) | MU-15Blocker |

PCR Materials & Methods

This experiment comprised nine individual PCR reactions. Variable factors examined within the set of nine reactions included the presence or absence of PEI derivatized Sepharose beads (approximately 25,000 PEI-Sepharose beads), the presence or absence of plasmid template (pKRASWT or pKRASMU(31) at 100 fmole per 50 μL reaction (0.4 nM)) and the presence or absence of 400 pmole of PNA Blocker Probe (MU-15Blocker, See: Table 2). The total volume of the PCR reactions including glycerol and beads was 50 μL.

Table 5, summarizes the composition of various tubes with respect to these variable factors. In addition, each PCR reaction contained 45 pmole of the KRAS 5' primer, 5 pmole of the KRAS 3' primer (See: Table 1), 3 mM MgCl$_2$, 250 μM NTPs, 2.0 units AmpliTaq DNA polymerase, 50 mM KCl, 10 mM TRIS-HCl pH 8.3, 50 pmole BK.RAS-Cy3 (See: Table 2) non-nucleotide probe (Linear Beacon), 1.5 μL of glycerol and 0.5 μL of Sepharose beads or water (control). The glycerol overlaid the beads to temporarily shield the them from the reaction components in the early stages of PCR so that the process would not be substantially inhibited by electrostatic binding of the primers to the matrix (beads) during the critical early thermocycles. During preparation and prior to PCR, the tubes were carefully handled to avoid mixing of components.

The PCR protocol involved a 20 second warm up to 95° C. (1st round only), followed by denaturing at 95° C. for 5 seconds, annealing at 55° C. for 30 seconds, and extension at 74° C. for 30 seconds. The denaturation-annealing-extension cycle was repeated for 30 cycles.

Post PCR Workup/Analysis

Figure 3:
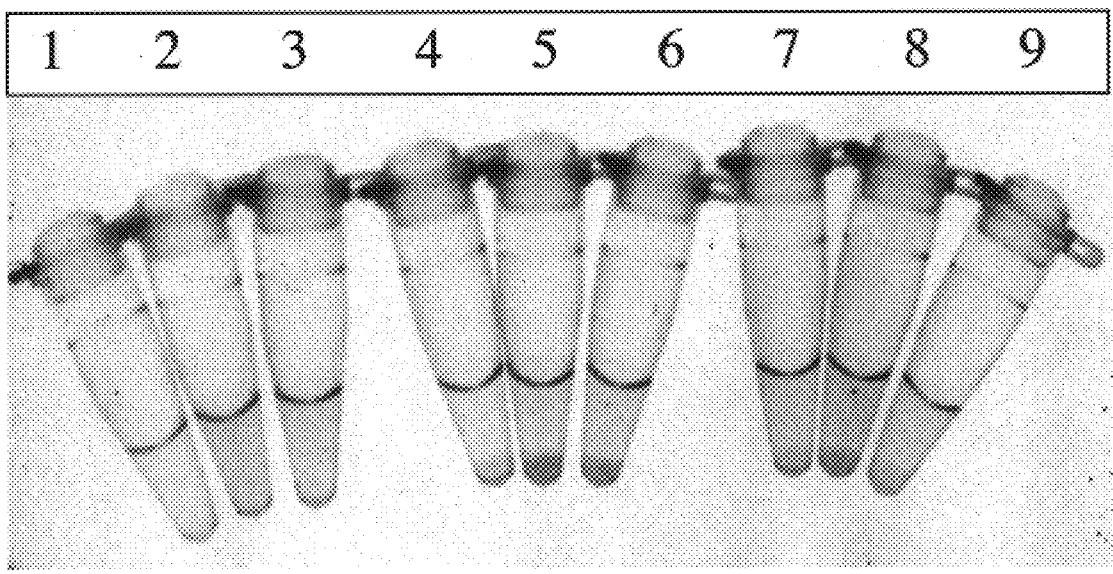
FIG. 3 is a computer generated negative of an image of a photograph of tubes from an experiment using PCR to generate different amplicons having a point mutation of a target sequence to which a Linear Beacon hybridizes to generate detectable signal.

After PCR, tubes 1–9 were placed on a transilluminator to visualize fluorescence and then photographed. FIG. 3 is a negative of the scanned image of the photograph taken of the nine mini-eppendorf tubes immediately after PCR (tubes are labeled 1–9).

Figure 4A:
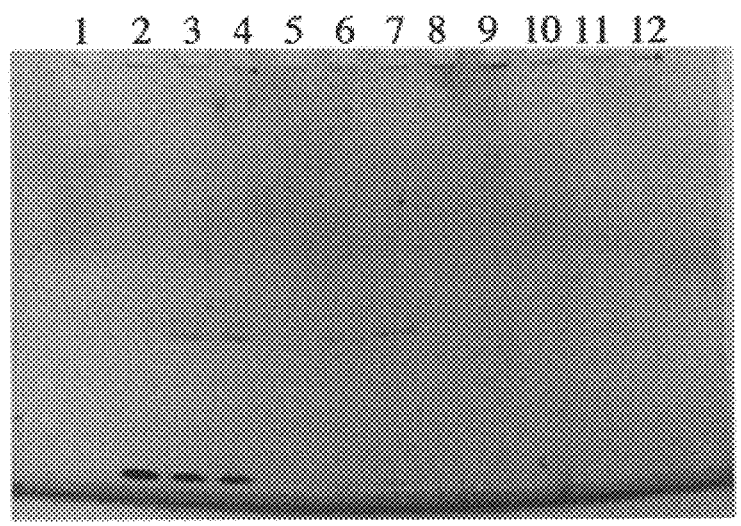
FIGS. 4A and 4B are computer generated negatives of an image of a photograph of the same polyacrylamide gel used to analyze the content of tubes shown in FIG. 3, before (FIG. 4A) and after (FIG. 4B) ethidium bromide staining.
Figure 4B:
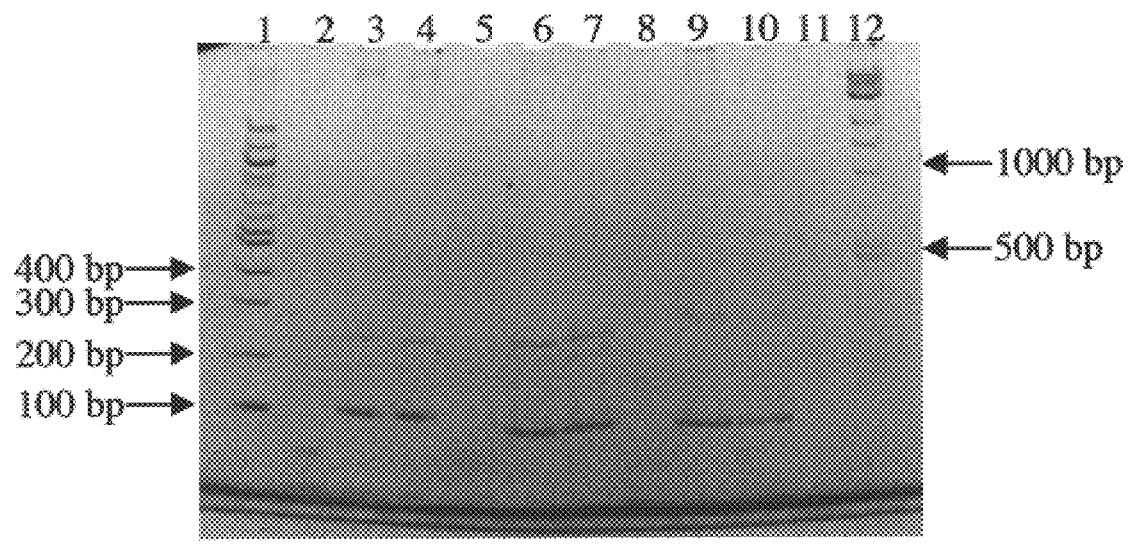

After photographing, the tubes were vortexed briefly, then centrifuged briefly to concentrate the beads. The supernatants were removed and the beads were washed with 100 μL 50 mM NaCl, 100 mM TRISCl pH 7.6. The electrostatically bound nucleic acids were then released from the beads for analysis by vortexing in 10 μL of a solution containing 100 mM CAPSO pH 10.7 and 2 M NaCl. The solution was then separated from the beads and 9 gL of each of the recovered solutions was combined with 3 μL of 4×loading dye. A sample from each tube was then run on a 10–20% gradient gel to confirm nucleic acid amplification and identify product size. FIGS. 4A and 4B are the negative of the images of photographs of the same 10–20% gradient polyacrylamide gel illuminated on a UV transilluminator which were taken before (FIG. 4A) and after (FIG. 4B) ethidium bromide staining.

Results

Tube Images/photographs

With reference to FIG. 3, tube 1 was a negative control containing no template and as expected, is not fluorescent after PCR (the tube contents resemble the background in the negative of the image). However, the contents of tubes 2 and 3 were visibly fluorescent under the transilluminator (darker than tube 1 in the negative of the image). This was the expected result for tube 2, since amplification of the template should have produced the 111 bp amplicon containing a target sequence to which the Linear Beacon is perfectly complementary. However, the amplicon generated in tube 3 contained a sequence containing a point mutation of the wild type amplicon. However, in the absence of the blocker probe, the Linear Beacon probe will at least partially hybridize to the mutant amplicon generated from plasmid pKRASMU(31) under the hybridization conditions present since the mutant and wild type amplicons are so closely related. Partial hybridization causes enough fluorescent signal generation to be visible to the eye under the transilluminator. Since no Sepharose beads were present in tubes 2 and 3, the orange color (darkness of the negative image) of the hybridized Linear Beacons is evenly distributed throughout the solution. Because the signal was not concentrated it did not produce a strong signal in the Figure.

The reagent composition of tubes 4 through 6 are identical to tubes 1 though 3, respectively, except that PEI-Sepharose beads were present during the PCR reaction. With reference to FIG. 3, tube 4 was a negative control containing no template and as expected, the solution and Sepharose beads are not fluorescent after PCR as compared with tubes 5 and 6 (the tube contents and beads resemble the background in the negative of the image). With reference to tubes 5 and 6, the Sepharose beads at the bottom of the tubes have become highly fluorescent with the intensity of tube 5 being slightly more intense as compared with tube 6. This result is as expected since amplification of the template should have produced the 111 bp amplicon (electrostatically bound to the bead matrix) to which the Linear Beacon hybridized to generate detectable signal. The fluorescent intensity of tube 6 is lower since the Linear Beacon is not perfectly complementary to the amplicon but can at least partially hybridize to generate detectable signal under the hybridization conditions present. Because there is little difference between tubes 5 and 6, visual inspection of the tubes however, does not allow one to confirm whether or not the sample contained mutant or wild type target sequence and is therefore not necessarily suitable for single point mutation analysis.

Upon comparison of tubes 2 and 3 with the intensity of signal from tubes 5 and 6, it becomes clear that concentration of the detectable fluorescent signal on the beads allows one to more clearly detect a positive result since the beads in tubes 5 and 6 are more clearly positive as compared with the solutions in tubes 2 and 3.

The reagent composition of tubes 7 through 9 are identical to tubes 4 though 6, respectively, except that in tubes 7–9, 400 pmole of MU15Blocker probe was added prior to PCR amplification. With reference to FIG. 3, tube 7 was a negative control containing no template and as expected, the Sepharose beads are not fluorescent after PCR as compared with tubes 8 and 9 (the tube contents and beads resemble the background in the negative of the image). Because the blocker probe is present, only the beads in tube 8 are clearly fluorescent as compared with the contents of tubes 7 and 9. Thus, visual inspection of the tubes will allow one to confirm whether or not the sample contained mutant or wild type target sequence. Therefore, this self-indicating assay is suitable for single point mutation/discrimination analysis. It will be appreciated by those of ordinary skill in the art that quantitation of detectable signal can be achieved by using an instrument, such as a flow cytometer, and no more than routine experimentation.

In summary, the data presented in FIG. 3 indicates that it is possible to perform homogeneous or closed tube amplification assays wherein signal of a probe can be concentrated on a matrix to which an amplified target nucleic acid is electrostatically immobilized. Furthermore, when utilizing blocker probes, the assay can be used for single point mutation analysis.

Gel Photographs/images

Analysis of the PCR reactions by gel was performed to determine the presence and size of amplicons to thereby confirm that the visual analysis of the tubes correlated with expected products of PCR amplification.

With reference to FIGS. 4A and 4B, the wells of the gel are at the top of the photographs. The images in FIGS. 4A and 4B are not directly comparable since the photographs were made using different exposure parameters. Aliquots of each tube were added near the top of the gel and electrophoretically directed towards the bottom of the gel. Lanes 1 and 12 contain two different double stranded DNA size markers; lane 1 is 100 bp ladder (New England BioLabs #323-1L) and lane 12 is a 1000 bp ladder (New England BioLabs #323-2S). Band sizes are indicated in FIG. 4B. Lanes 2–4 contain 9 µL of samples 1–3 respectively, lanes 5–10 contain samples of released nucleic acid isolated from the beads in tubes 4 through 9 respectively, and lane 11 is a blank.

With reference to FIG. 4A, the presence of inherently fluorescent bands can be seen in lanes 3, 4, 6, 7, and 9 (from samples 2, 3, 5, 6 and 8 respectively) toward the bottom, and in the middle of the image. The fluorescent bands at the bottom of the image are most likely probe molecules which have migrated into the gel. The fluorescent bands in the middle of the image can be attributed to the presence of the Linear Beacon still hybridized to the nucleic acid amplicon even after it has migrated into the gel. This result is consistent with amplification in tubes 2, 3, 5, 6 and 8 as was indicated by the visual analysis and photographing of the tubes. By comparison, there are no visible fluorescent bands in any of lanes 2, 5, 8, and 10 (tubes 1, 4, 7 and 9). This result is consistent with the lack of fluorescence observed in these tubes.

With reference to FIG. 4B, all nucleic acid is fluorescent because it is stained with ethidium bromide. Therefore, the size markers in lanes 1 and 12 are now visible. Strong fluorescent bands having a size consistent with the expected 111bp product are visible in lanes 3, 4, 6, 7, 9 and 10 (tubes, 2, 3, 5, 6, 8 and 9) but are absent in lanes 2, 5, and 8 (tubes 1, 4 and 7). This data confirms production of the intended amplicons in tubes 2, 3, 5, 6, 8 and 9 and further confirms that the nucleic acid was recovered from material originally electrostatically bound to the Sepharose beads. Most noteworthy is the presence of a bands in both lanes 8 and 10 (tubes 7 and 9). These bands confirm that amplification occurred in these samples. Therefore the lack of signal in tube 9 as compared with tube 7 can only be attributable to the presence of the blocker probe which allow one to achieve point mutation discrimination of the amplicon.

In summary, the data presented in FIGS. 4A and 4B, when considered with the data presented in FIG. 3, conclusively demonstrate that it is possible to perform self-indicating probe-based assays suitable for single base discrimination (single point mutation discrimination) wherein signal of a probe can be concentrated on a matrix to which an amplified target nucleic acid is electrostatically immobilized.

Example 13

Comparison of Assay Operating Range for PNA:DNA and DNA:DNA Hybrids

This example is designed to compare the operating range for electrostatic binding of non-nucleotide probes (e.g. PNA) with that of the most nearly equivalent nucleic acid probes in an electrostatic binding assay for a nucleic acid target molecule which is nearly equivalent in size to the probe. The goal is therefore to determine a range of ionic strength under which the non-nucleotide and polynucleotide probes will bind to the matrix only if the nucleic acid target is present. For this example, a PNA probe (WT-15Flu PNA; See Table 2) and a DNA probe (WT-15Flu; See Table 1) was diluted in water to a concentration of 5 µM. The nucleic acid target (KRASWT(21); See Table 1) was also diluted in water to a concentration of 50 µM.

TABLE 6

Salt Buffers:

| Buffer ID | Buffer Components: |
| --- | --- |
| G | 0 mM NaCl, 10 mM TRIS-Cl pH 8.0 |
| H | 100 mM NaCl, 10 mM TRIS-Cl pH 8.0 |
| I | 200 mM NaCl, 10 mM TRIS-Cl pH 8.0 |
| J | 300 mM NaCl, 10 mM TRIS-Cl pH 8.0 |
| K | 400 mM NaCl, 10 mM TRIS-Cl pH 8.0 |
| L | 500 mM NaCl, 10 mM TRIS-Cl pH 8.0 |
| M | 600 mM NaCl, 10 mM TRIS-Cl pH 8.0 |
| N | 700 mM NaCl, 10 mM TRIS-Cl pH 8.0 |

Next, four sets of eight eppendorf tubes were prepared with 100 µL of each of the eight salt buffers described in Table 6. The four sets of tubes comprised the following experimental conditions: Into Set I was added the PNA probe but no nucleic acid target (KRASWT(21)). This is the "no target" control. Into Set II was added the PNA probe and the nucleic acid target (KRASWT(21)). Into Set III was added the DNA probe but no nucleic acid target (KRASWT (21). This is the "no target" control. Into Set IV was added the DNA probe and the nucleic acid target (KRASWT(21).

These samples were prepared by adding one microliter of the appropriate stock of PNA probe or DNA probe to each tube in Sets I, II, III and IV to thereby achieve a final concentration of 250 nM probe. To each tube in Sets II and IV was also added one microliter of the stock of nucleic acid target (KRASWT(21) to thereby create a sample having a final concentration of 2.5 µM target. To the "no target" control Sets I and III, one microliter of water was added.

All tubes were vortexed briefly to mix the ingredients, and held at room temperature for approximately 5 minutes to allow hybridization of the probes and targets. To each tube was then added one microliter of PEI Sepharose particles suspended in water. The tubes were vortexed briefly, allowed to stand at room temperature for approximately 5 minutes, then centrifuged for 30 seconds to concentrate the particles at the bottom.

Tubes were then arranged over a UV light source (transilluminator) and photographed. The negative image of the photograph is presented as FIG. 5. Supernatants were then removed and discarded. Next, 100 μL of the appropriate salt buffer was added back to the appropriate tubes. The PEI particles were resuspended in the hybridization buffer by vortexing vigorously and then each suspended particle sample was transferred to an individual well in a microtiter plate. The samples in the microtiter plate were immediately analyzed (Wallac, Victor, 1420 Multilabel Counter, Gaithersburg, Md.). The results of the analysis of fluorescence on the beads is presented in Table 7.

Results

Tube Images/photographs

With reference to FIG. 5, the four sets of tubes are arranged in order from top to bottom. Within each set, the tubes are arranged in order of increasing salt concentration from left to right. For example, the tube closest to the upper left corner of the Figure is Set I, Buffer G (0.0 M NaCl), and the tube nearest the lower right corner is Set IV, Buffer N (0.7 M NaCl).

With reference to FIG. 5, Set I, the lack of fluorescent signal at the bottom of the tube indicates that the PNA probe has very little affinity for the particles in the absence of the nucleic acid target (KRASWT(21). In Set II by comparison, the PNA probe is concentrated on the matrix to a salt concentration of approximately 300 mM (See Salt Buffer J). This result is consistent with hybridization of the probe to the target sequence electrostatically bound to the matrix. The lack of probe concentrated on the matrix at salt concentrations above 300 mM is likely due to the lack of binding of the short nucleic acid target (KRASWT(21) at those salt concentrations. Taken as a whole, the data indicates that the PNA probe does not interact with the matrix under any conditions of ionic strength examined. Thus, the applicable range for the assay utilizing this PNA probe is at least 0–700 mM salt.

With reference to FIG. 5, Set III, the DNA probe is substantially concentrated on the matrix up to a salt concentration of approximately 300 mM (See Salt Buffer I) and weakly up to a salt concentration of 400 mM (See Salt Buffer K). This data indicates that the native DNA probe has a substantial inherent affinity for the matrix. By comparison, Set IV, indicates that the probe/target sequence hybrid raises the presence of probe strongly concentrated on the matrix up to a salt concentration of approximately 400 mM (See Salt Buffer K) and weakly up to a salt concentration of 500 mM (See Salt Buffer L). Therefore the operating range for discriminating probe from probe/target sequence complex when using this all DNA system is approximately 300 to 500 mM salt. This a very narrow operating range by comparison with the PNA probe. Note: The apparent conflict between the results of Experiment 9 and the results described above, wherein the PNA probe WT-15Flu detectably binds to the matrix up to 100 mM salt (Exp. 9) but does not interact with the support even in 0 mM salt, has been confirmed to be condition dependent. The buffer in Experiment 9 contains Tween-20 which appears to promote the interaction of the PNA probe with the support. Additionally, the PNA probe in this experiment was first added to water from the concentrated stock of 1/1 DMF:water which appears to decrease the interaction of the PNA probe with the support. To avoid doubt, all data is consistent with the fluorescein label being the primary source of interaction with the matrix which was an apparent result of Experiment 9.

Quantitation of Particle Associated Fluorescence

The visual comparison of the tube was also confirmed by quantitative analysis of fluorescence of the resuspended beads. The quantitative fluorescence measurements as well as derived data for the beads is presented in Table 7.

With reference to Table 7, the raw fluorescent reading from each sample (Sets I–IV; rows B–E, respectively) of suspended particles at each of the salt buffers (Buffers G–N; columns 2–9, respectively) is presented. From this data the signal to noise data for PNA probe (row F) and DNA probe (row G) is mathematically derived from the raw fluorescence data. For example, the raw fluorescent value obtained for Buffer G in Set I (column 2, row B=738 rlu) was divided into the raw fluorescent value of Buffer G in Set II (column 2, row C=12736 rlu) to obtain the S/N value for the PNA probe in Buffer 0 of 17.3 rlu (12736÷738 =17.3 (column 2 row F)).

TABLE 7

Bead Fluorescence Data

| | 1 | 2 | 3 | 4 | 5 | 6 | 7 | 8 | 9 |
|---|---|---|---|---|---|---|---|---|---|
| A | Buffer # | G | H | I | J | K | L | M | N |
| B | Set I | 738 | 652 | 618 | 956 | 696 | 1052 | 992 | 1124 |
| C | Set II | 12736 | 12052 | 11212 | 8610 | 1726 | 830 | 420 | 660 |
| D | Set III | 36422 | 39807 | 33577 | 28001 | 7572 | 5750 | 5286 | 4640 |
| E | Set IV | 36170 | 47133 | 46570 | 43731 | 43495 | 13020 | 2284 | 1710 |
| F | PNA S/N | 17.3 | 18.5 | 18.1 | 9.0 | 2.5 | 0.8 | 0.4 | 0.6 |
| G | DNA S/N | 1.0 | 1.2 | 1.4 | 1.6 | 5.7 | 2.3 | 0.4 | 0.4 |

The signal to noise ratio calculated from the quantitative raw fluorescence data for the PNA probe agrees with the visual analysis. A strong signal can be detected above the background from 0–300 mM salt (See: row F, columns 2–5). By comparison, only a weak signal is detected for the DNA probe at salt concentrations of between 300 and 500 mM (See: row G, columns 5–7).

Taken as a whole the visual data of FIG. 5 and the quantitative data of Table 7 clearly demonstrates that the non-nucleotide PNA probes operate within a substantially greater range of salt concentrations as compared with the most nearly equivalent DNA probes when used in an electrostatic immobilization assay. The PNA probes also provide a substantially greater signal to noise ratio as compared with the DNA probes. Consequently, the data indicates several advantages which make the PNA probes the superior choice for performing probe-based analysis of nucleic acid electrostatically immobilized to a matrix.

Example 14

Single Point Mutation Discrimination Using a Protection/Digestion Assay

This experiment was designed as a Protection/Digestion Assay suitable for single point mutation discrimination. As designed, the assay also demonstrates a means for improving the assay caused by adjusting the temperature of the assay to a point where non-specific hybrids begin to melt and the nucleic acid which thereby causes the non-specific signal now becomes available as a substrate to the enzyme. Digestion of the interfering non-target sequence results in a substantial improvement in signal to noise ratio of the assay. The assay was also substantially simplified by use of a self-indicating Linear Beacon (BK.RAS-Cy3; See Table 2) and electrostatic immobilization of the Linear Beacon/target sequence hybrid to Sepharose particles which enabled the rapid electrostatic capture and quantitation of the Linear Beacon/target sequence hybrid.

Materials

Mung Bean Nuclease and 10×buffer were obtained from New England BioLabs. The enzyme is supplied at 10 units per microliter. When the 10×buffer is diluted according to the manufactures instructions, the buffer contains 50 mM sodium acetate, 30 mM sodium chloride, 1 mM zinc chloride and has a pH of 5.0 at 25° C.

Experimental

This experiment comprised 6 samples in which the PNA probe was hybridized to either the KRASWT(24) target (See: Table 1) or the single base mismatch, KRASMU(24) target (See: Table 1). A no target control and control samples without enzyme were also performed. The assay was performed at 65° C. This temperature is below the Tm of the perfect complement (BK.RAS-Cy3/KRASWT(24)) which has been measured to be approximately 81° C. and very close to the Tm of the imperfect complement (BK.RAS-Cy3/KRASMU(24)) which has been measured to be approximately 67° C. under identical conditions. This temperature is within the range of five degrees above and ten degree below the melting temperature of the imperfect complement which is being discriminated in the assay and which has a single point mutation as compared with the target sequence KRASWT(24). The composition of the six samples is summarized below:

Sample 1. KRASWT(24) target, + enzyme
Sample 2. KRASMU(24) target, + enzyme,
Sample 3. No Target+ enzyme
Sample 4. KRASWT(24) target, no enzyme
Sample 5. KRASMU(24) target, no enzyme,
Sample 6. No Target, no enzyme For this experiment, PNA probes and DNA targets were added to a final concentration of 0.33 μM in a 100 μL volume of 1×mung bean nuclease buffer. Samples were heated to 95° C. for 5 minutes to denature hybrids and then cooled to 65° C. After 5 minutes of equilibration at 65 ° C., samples 1–3 were treated with 0.3 μL mung bean nuclease. Samples 4, 5 and 6 were not treated with nuclease. All samples were vortexed briefly, then allowed to incubate for 10 minutes at 65° C. After the incubation, all samples were treated with 1 μL of PEI Sepharose particles, vortexed vigorously, then centrifuged for 30 seconds to pellet the particles. Supernatants were removed and the particles were resuspended in 100 μL 1×mung bean nuclease buffer. The entire contents of each tube was transferred to a microtiter plate and analyzed for fluorescence using a Wallac, Victor, 1420 Multilabel Counter. Fluorescence values are described in relative light units (rlu).

Results

Fluorescent measurements of the two "no target" controls, sample #3 and sample #6, gave similar values, as would be expected (400 and 466 rlu respectively). The "no target" values were subtracted from the raw fluorescent values of the other samples to obtain values minus background signal. The values minus background signal for the remaining samples were as follows; sample #1, (4926 rlu); sample #2, (338 rlu); sample #4, (8896 rlu); and sample#5, (2532 rlu).

Comparison of enzyme treated and untreated samples reveals the relative benefits of nuclease treatment. Comparison of sample #1 and sample #4 demonstrates a 45% loss of signal from the complimentary target, KRASWT(24), when treated with the nuclease ((8896–4929)÷8896=45%). In contrast, comparison of sample #2 with sample #5 demonstrates an 87% loss of signal from the single base mismatch target, KRASMU(24), from enzyme treatment ((2532–338)÷2532)=87%). As a result of the differential loss in signal from the imperfect complement as compared with the perfect complement, which is attributable to enzymatic digestion, there is a corresponding increase in signal to noise ratio (fully complimentary signal divided by mismatch signal, S/N) for the assay. The S/N value for the sample which was not treated with enzyme was 3.5 (8896÷2532=3.5) and the S/N value for the sample which was treated with enzyme was 14.6 (4926÷338=14.6). Though a loss of specific signal was observed in the enzyme treated samples (compare raw fluorescence for sample #'s 1 and 2 with 4 and 5, respectively), the net gain in signal to noise was very beneficial to the overall performance of the assay.

Taken as a whole, this data demonstrates that the Protection/Digestion Assay can be combined with electrostatic immobilization of the non-nucleotide probe/target sequence complex to provide a rapid result. The non-nucleotide probe can be a Linear Beacon and the assay self-indicating. Additionally, the result of the assay can be substantially enhanced by judicious modulation of assay temperature to thereby melt and digest nucleic acid which caused false positive results.

Example 15

Array Assay

For this assay, a commercially available microscope slide having a cationic surface was used to electrostatically immobilize premixed samples containing nucleic acid and probe which had been deposited on the slide into an array of spots. The microscope slide was then washed to remove unhybridized probe and detect the target sequence if present on the microscope slide.

Preparation of Probe Targets, and Particles

The cyanine-3 (Cy3) labeled PNA 15-mer (RASWT-Cy3), in a solution of 50% aqueous N,N-dimethylformamide at a concentration of 570 pmol/μL, was diluted to a concentration of 20 pmol/μL in hybridization buffer (12% aqueous formamide, 5 mM Tris hydrochloride, 25 mM sodium chloride and 0.05% SDS at a pH of 7.5). The DNA oligonucleotide 31-mer (KRASMU(31)), that was complementary to RASWT-Cy3, in water at a concentration of 20 pmol/μL was diluted 221 fold to a concentration of 1 pmol/μL in hybridization buffer. The DNA oligonucleotide 60-mer (CompDNA), that was non-complementary to RASWT-Cy3, in water at concentration of 90 pmol/μL, was diluted 90 fold to a concentration of 1 pmol/μL in hybridization buffer.

Hybridization, Spotting and Data Acquisition

Tube A: In a microfuge tube was combined 1 μL of water with 1 μL of RASWT-Cy3 and 18 μL of hybridization buffer.

Tube B: In a microfuge tube was combined 1 µL of KRASMU(31) with 1L of RASWT-Cy3 and 18 µL of hybridization buffer.

Tube C: In a microfuge tube was combined 1 µL of CompDNA with 1AL of RASWT-Cy3 and 18 µL of hybridization buffer.

Tubes A, B and C were incubated for 15 min at room temperature and then 0.2 µL of the solution from each tube was applied as a row of droplets to a GAPS Coated Slide (Corning, Corning N.Y.). The slide had a gamma-aminopropyl silane coated surface. The slide was placed, for a period of approximately 20 min, in an oven maintained at 50° C. until the spots had dried. The slide was cooled to room temperature and imaged to verify the location of the spots on the slide. A Genetic Microsystems array microimager (GMS 318, Woburn, Mass.) was used to acquire slide images using the green laser according to the manufacturer's instructions. The slide was then removed from the imager and washed with hybridization buffer in a small tray with gentle agitation for 5 min at room temperature. The slide was then rinsed with deionized water, shaken to remove excess water, and allowed to dry on the bench. The image of the washed slide was again acquired.

Results

Figure 6A:
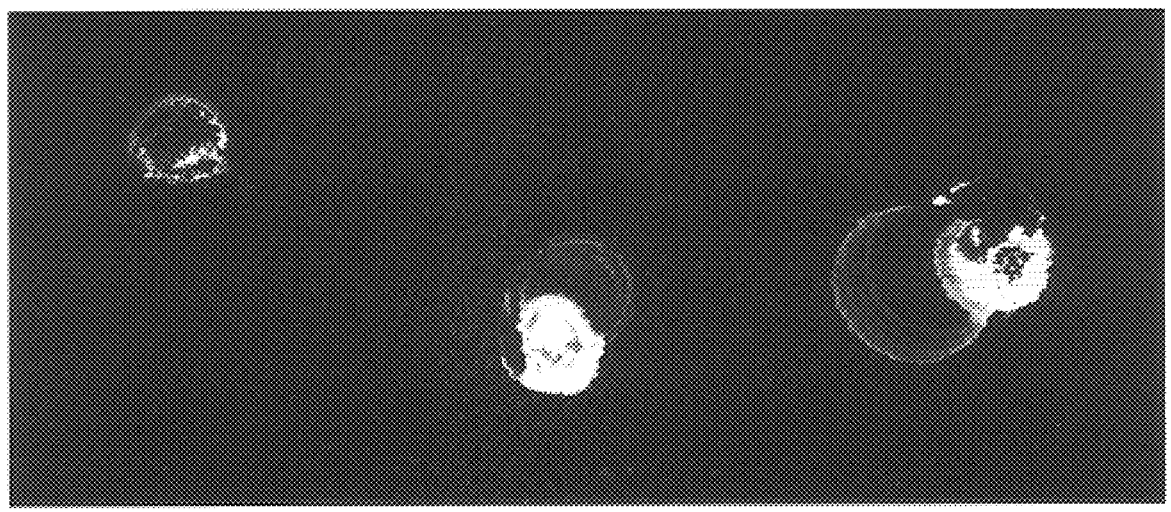
FIGS. 6A and 6B are images of the same GAPS coated microscope slide containing spotted samples, before (6A) and after (6B) washing to remove material not otherwise electrostatically immobilized.
Figure 6B:
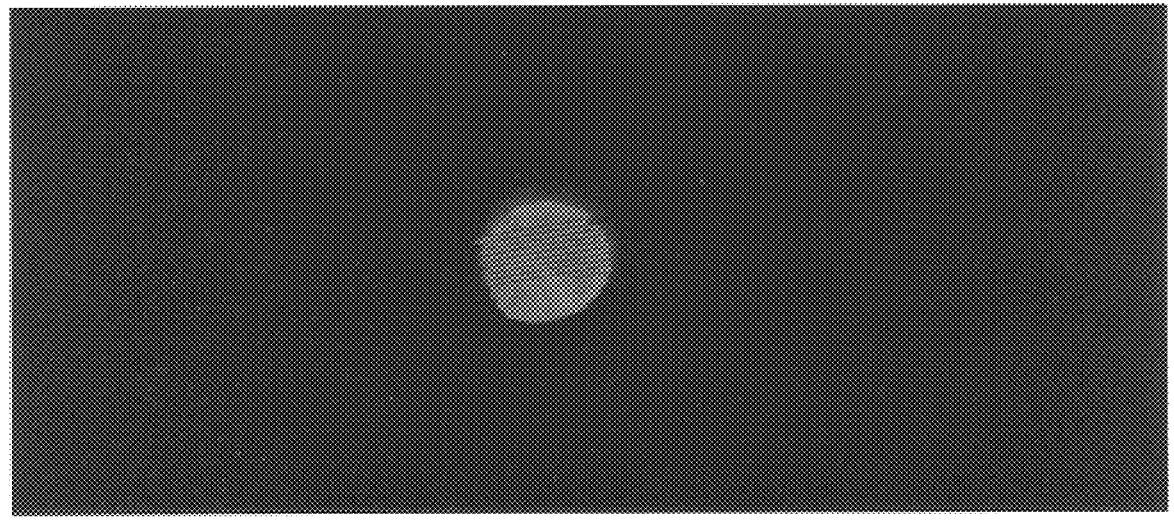

FIGS. 6A and 6B are the images of the slide taken before and after the wash step, respectively. Prior to washing there were three visible spots labeled A, B & C, corresponding to the reactions from Tubes A, B & C. However, after the wash step (FIG. 6B), Spot A was no longer visible to the instrument. This demonstrates that the PNA probe, in the absence of any nucleic acid, was removed from the slide surface by the wash step. When the complementary target KKRASMU (31) was present, the visible signal at the array location was retained (Spot B), presumably due to hybridization of the probe to the electrostatically immobilized target. When a noncomplementary nucleic acid was used, most of the PNA probe was washed away (Spot C). Taken as a whole, the data demonstrates that it is possible to prepare a matrix array of electrostatically immobilized nucleic acid and easily assay for the presence of a target sequence located thereon using a non-nucleotide probe.

Example 16

Line Assay

In the example, a line assay is performed wherein a non-nucleotide probe/target sequence complex is captured using a line of polycationic polymer on a commercially available membrane material wherein reagents are allowed to wick into the membrane as is typical of a lateral flow assay.

Preparation of Membrane

Strips (2.5 cm×20 cm) of Millipore membrane (P/N WOPP, Bedford, Mass.) were wet in a solution of 0.5% glutaraldehyde in ethanol. The wet strips were placed on a piece of Whatman 3MM paper in a fume hood. After 3 minutes, when the filter strips appeared dry, they were removed from the hood and place on the platen of an Ivek microstriper (Ivek Corp., Springfield, Vt.). A 3 mm wide line of polyethylenamine (PEI) solution was then applied along the midpoint of each membrane strip. The PEI solution was previously prepared by dissolving 750,000 molecular weight PEI (Aldrich Chemical, Milwaukee, Wis.) in water and adjusting the pH to 8.5 with dilute hydrochloric acid. The PEI solution was then diluted to a final concentration of 1 mg of PEI per milliliter.

Once the filter strips were striped with the PEI solution, they were allowed to dry overnight on the bench. The next day the strips were washed with dilute hydrochloric acid, pH~3, for 45 minutes. The strips were then washed with water and placed on Whatman 3MM paper to dry for 24 hrs. The strips were cut into smaller pieces 1 cm wide by 2.5 cm long such that each strip had a PEI line across its mid point. At one end, 5 mm of each piece was sandwiched between two pieces of Whatman 3MM paper (2×1 cm) using a small metal Bulldog clamp.

Preparation of Probe, Targets, and Particles

A biotinylated PNA 15-mer (BioP-15), in a solution of 50% aqueous N,N-dimethylformamide at a concentration of 333 pmol/µL, was diluted 333 fold to final concentration of 1 pmol/µL into hybridization buffer (50% aqueous formamide, 20 mM Tris hydrochloride, 100 mM sodium chloride and 0.1% SDS, pH of 7.5). The DNA oligonucleotide 60-mer (CompDNA; See Table 1), complementary to BioP-15 in water at a concentration of 90 pmol/µL, was diluted 90 fold to a concentration of 1 pmol/µL in hybridization buffer. A DNA oligonucleotide 60-mer (NonCompDNA; See Table 1) that was non-complementary to BioP-15, in water at a concentration of 221 pmol/µL, was diluted 221 fold to a concentration of 1 pmol/µL in hybridization buffer. A suspension of streptavidin gold particles (Arista Biologicals, Inc., Bethlehem, Pa.)), 40 nm diameter, was diluted 20-fold with hybridization buffer.

Hybridization

Tube A: In a microfuge tube was combined 2.5 µL of CompDNA with 2.5 µL of BioP-15. The reaction was then incubated for 2 min at room temperature and 20 µL of 40 nm streptavidin gold particles in hybridization solution was added.

Tube B: In a microfuge tube was combined 2.5 of µL NonCompDNA with 2.5 µL of BioP-15. The reaction was then incubated for 2 min at room temperature and 20 µL of 40 nm streptavidin gold particles in hybridization solution was added.

Line Assay

Tubes A and B were then incubated for 15 min at room temperature after addition of the gold particles. The contents of the tubes were transferred onto a small piece of Parafilm lab film (American Can Company). Onto different pieces of Parafilm were spotted two 20 µl droplets of hybridization buffer. Into each drop was dipped the end of a membrane strip such that the buffer wicked towards the end held by the Bulldog clamp. The filter strips were held in contact with the liquid until entire droplet had wicked into the membrane. The ends of the two strips were then dipped separately into the contents of Tube A or Tube B that had previously been transferred to clean sections of the lab film. Once the entire A and B droplets had been wicked into their respective filter strips, the filter ends were then separately dipped into 10 µL droplets of hybridization buffer.

Results

In the case of Tube A that contained the BioP-15 and its DNA complement CompDNA, a red line formed across the filter strip during the wicking of the Tube A contents into the filter strip. In the case of Tube B, no line was seen. The results demonstrate the feasibility of a simple line assay for detecting nucleic acids using a cationic polymer as a capture zone on the membrane filter.

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

We claim:

1. A composition comprising:
   a) a matrix;
   b) at least one nucleic acid molecule, comprising at least one target sequence, that is electrostatically bound to said matrix under suitable electrostatic binding conditions; and
   c) at least one non-nucleotide probe comprising a probing nucleobase sequence that is sequence specifically hybridized to at least a portion of the one or more target sequences to thereby form a non-nucleotide probe/target sequence complex and wherein the backbone of the non-nucleotide probe or probes is sufficiently neutral or positively charged, under electrostatic binding conditions that it exhibits little or no affinity for the matrix.

2. The composition of claim 1, wherein said matrix is selected from the group consisting of:
   a) a solution insoluble polymer;
   b) a surface;
   c) a beaded support;
   d) a porous beaded support;
   e) a cast polymer;
   f) a co-polymeric material; and
   g) a gel;
wherein said matrix comprises charged functional groups that are suitable for binding nucleic acid under electrostatic binding conditions.

3. The composition of claim 2, wherein said matrix is beaded anion exchange media.

4. The composition of claim 1, wherein the non-nucleotide probe or probes are unlabeled.

5. The composition of claim 4, wherein to the non-nucleotide probe/target sequence complex is directly or indirectly linked a detectable antibody.

6. The composition of claim 5, wherein the non-nucleotide probe or probes are peptide nucleic acid.

7. The composition of claim 1, wherein the composition is formed at one or more positions on an array.

8. The composition of claim 1, wherein the one or more nucleic acid molecules have been degraded except for that portion of the molecule or molecules that are protected from degradation by hybridization to the non-nucleotide probe.

9. The composition of claim 1, wherein the matrix is formulated into a line or shape on a support.

10. The composition of claim 9, wherein composition is formed in a lateral flow assay device.

11. The composition of claim 1, wherein said target sequence or sequences are characteristic for the detection of an organism, virus, fungi or pathogen sought to be detected in an assay.

12. The composition of claim 1, wherein said target sequence or sequences are characteristic for the detection of a genetically-based disease or is characteristic for the detection of a predisposition to a genetically-based disease.

13. The composition of claim 1, wherein electrostatic binding occurs by salt pair formation between charged groups of the nucleic acid backbone and charged groups of the matrix.

14. The composition of claim 1, wherein the non-nucleotide probe or probes comprises a completely neutral backbone under electrostatic binding conditions.

15. The composition of claim 14, wherein the non-nucleotide probe or probes are peptide nucleic acids.

16. The composition of claim 1, wherein the non-nucleotide probe or probes are labeled with at least one detectable moiety.

17. The composition of claim 16, wherein the labeled non-nucleotide probe or probes are non-nucleotide "Beacon" probes.

18. The composition of claim 16, wherein one or more detectable moieties are selected from the group consisting a chromophore, a fluorochrome, a spin label, a radioisotope, an enzyme, a hapten and a chemiluminescent compound.

19. The composition of claim 18, wherein the enzyme is selected from the group consisting of alkaline phosphatase, soybean peroxidase and horseradish peroxidase.

20. The composition of claim 18, wherein the hapten is selected from the group consisting of fluorescein, biotin, 2,4-dinitrophenyl and digoxigenin.

21. The composition of claim 1, wherein said probing nucleobase sequence is substantially complementary to the target sequence.

22. The composition of claim 1, wherein said probing nucleobase sequence is exactly complementary to the target sequence.

23. A composition comprising:
   a) a matrix;
   b) at least one nucleic acid molecule, comprising at least one target sequence, that is electrostatically bound to said matrix under suitable electrostatic binding conditions; and
   c) at least one self-indicating non-nucleotide probe comprising a probing nucleobase sequence that is sequence specifically hybridized to at least a portion of the one or more target sequences to thereby form a non-nucleotide probe/target sequence complex and wherein the backbone of the self-indicating non-nucleotide probe or probes is sufficiently neutral or positively charged, under electrostatic binding conditions, that it exhibits little or no affinity for the matrix.

24. A composition comprising:
   a) a matrix array of at least two nucleic acid molecules, at least one of which comprises a target sequence, that are electrostatically bound at unique locations to said matrix under suitable electrostatic binding conditions; and
   b) at least one non-nucleotide probe comprising a probing nucleobase sequence that is sequence specifically hybridized to at least a portion of any one or more target sequences electrostatically immobilized to the matrix to thereby form non-nucleotide probe/target sequence complexes at said unique locations and wherein the backbone of the non-nucleotide probe or probes is sufficiently neutral or positively charged, under electrostatic binding conditions, that it exhibits little or no affinity for the matrix.

25. The composition of claim 24, wherein the non-nucleotide probe is a non-nucleotide "Beacon" probe.

26. The composition of claim 24, wherein the non-nucleotide probe or probes are unlabeled.

27. The composition of claim 26, wherein to the non-nucleotide probe/target sequence complex is directly or indirectly linked a detectable antibody.

28. The composition of claim 27, wherein the non-nucleotide probe or probes are peptide nucleic acid.

29. The composition of claim 24, wherein the non-nucleotide probe or probes are labeled with at least one detectable moiety.

30. The composition of claim 29, wherein one or more detectable moieties are selected from the group consisting a chromophore, a fluorochrome, a spin label, a radioisotope, an enzyme, a hapten and a chemiluminescent compound.

31. The composition of claim 30, wherein the enzyme is selected from the group consisting of alkaline phosphatase, soybean peroxidase and horseradish peroxidase.

32. The composition of claim 30, wherein the hapten is selected from the group consisting of fluorescein, biotin, 2,4-dinitrophenyl and digoxigenin.

33. A kit for the analysis of a sample containing a nucleic acid molecule comprising a target sequence, said kit comprising a matrix "at least one nucleic acid molecule having at least one target sequence that is electrostatically bound to said matrix under suitable electrostatic binding conditions," between "a matrix" and "and at least one non-nucleotide probe" and at least one non-nucleotide probe having a probing nucleobase sequence that sequence specifically hybridizes, under suitable hybridization conditions, to at least a portion of the target sequence sought to be detected in said sample and wherein the backbone of the non-nucleotide probe or probes is sufficiently neutral or positively charged, under electrostatic binding conditions that it exhibits little or no affinity for the matrix.

34. The kit of claim 33, further comprising one or more reagents suitable for modulating the electrostatic binding conditions of the assay.

35. The kit of claim 33, further comprising enzymes that degrade sample contaminants but not a non-nucleotide probe/target sequence complex.

36. The kit of claim 33, wherein the kit is used to detect organisms in food, beverages, water, pharmaceutical products, personal care products, dairy products or environmental samples.

37. The kit of claim 33, wherein the kit is used to test raw materials, products or processes.

38. The kit of claim 33, wherein the kit is used to examine clinical samples such as clinical specimens or equipment, fixtures and products used to treat humans or animals.

39. The kit of claim 33, wherein the kit is used to detect a target sequence that is specific-for a genetically-based disease or is specific for a predisposition to a genetically-based disease.

40. The kit of claim 33, wherein the kit is used to detect a target sequence in a forensic technique such as prenatal screening, paternity testing, identity confirmation or crime investigation.

41. The kit of claim 33, wherein the kit is used to perform a self-indicating assay.

42. The kit of claim 33, wherein the kit comprises two or more independently detectable non-nucleotide probes and is designed to perform a multiplex assay.

43. The kit of claim 42, wherein the two or more independently detectable non-nucleotide probes are non-nucleotide "Beacon" probes.

44. The kit of claim 33, wherein the non-nucleotide probe is a non-nucleotide "Beacon" probe.

* * * * *

```
                              SEQUENCE LISTING

<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<221> NAME/KEY: misc_feature
<222> LOCATION: (1)
<223> OTHER INFORMATION: 5' biotin label
<220> FEATURE:
<223> OTHER INFORMATION: Description of Artificial Sequence:synthetic
      probe, primer or target

<400> SEQUENCE: 1
gtggtagttg gagctggtgg cgta                                              24

<210> SEQ ID NO 2
<211> LENGTH: 24
<212> TYPE: DNA
<213> ORGANISM: Artificial Sequence
<220> FEATURE:
<221> NAME/KEY: misc_feature
<222> LOCATION: (1)
<223> OTHER INFORMATION: 5' biotin label
<220> FEATURE:
<223> OTHER INFORMATION: Description of Artificial Sequence:synthetic
      probe, primer or target

<400> SEQUENCE: 2
gtggtagttg gagcttgtgg cgta                                              24

<210> SEQ ID NO 3
<211> LENGTH: 31
<212> TYPE: DNA
<213> ORGANISM: Artificial Sequence
<220> FEATURE:
<221> NAME/KEY: misc_feature
<222> LOCATION: (1)
<223> OTHER INFORMATION: 5' biotin
<220> FEATURE:
<223> OTHER INFORMATION: Description of Artificial Sequence:synthetic
      probe, primer or target

<400> SEQUENCE: 3
gtggtagttg gagcttgtgg cgtaggcaag a                                      31

<210> SEQ ID NO 4
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: 5' fluorescein label
<220> FEATURE:
<223> OTHER INFORMATION: Description of Artificial Sequence:synthetic
      probe, primer or target

<400> SEQUENCE: 4
acgccaccag ctcca                                                        15

<210> SEQ ID NO 5
```

```
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: 5' fluorescein label
<220> FEATURE:
<223> OTHER INFORMATION: Description of Artificial Sequence:synthetic
      probe, primer or target

<400> SEQUENCE: 5
acgccacaag ctcca                                                      15

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 6
gcttgtttcg gcgtgggtat                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 7
taggttgagg ccgttgagca                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 8
atgactgaat ataaacttgt                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 9
ctctattgtt ggatcatatt                                                 20

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 10
tcactagtcc cttcaaggct agcagtataa tgggttctag gtaaacgttc caccgttact     60
```

-continued

```
<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 11
agtaacggtg gaacgtttac ctagaaccca ttatactgct agccttgaag ggactagtga      60

<210> SEQ ID NO 12
<211> LENGTH: 111
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 12
atgactgaat ataaacttgt ggtagttgga gcttgtggcg taggcaagag tgccttgacg      60
attcagctaa ttcagaatca ttttgtggac gaatatgatc caacaataga g             111

<210> SEQ ID NO 13
<211> LENGTH: 111
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 13
atgactgaat ataaacttgt ggtagttgga gctggtggcg taggcaagag tgccttgacg      60
attcagctaa ttcagaatca ttttgtggac gaatatgatc caacaataga g             111

<210> SEQ ID NO 14
<211> LENGTH: 111
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 14
ctctattgtt ggatcatatt cgtccacaaa atgattctga attagctgta tcgtcaaggc      60
actcttgcct acgccaccag ctccaactac acaagttta tattcagtca t              111

<210> SEQ ID NO 15
<211> LENGTH: 111
<212> TYPE: DNA
<213> ORGANISM: Artificial Sequence
<220> FEATURE:
<223> OTHER INFORMATION: Description of Artificial Sequence:synthetic
      probe, primer or target

<400> SEQUENCE: 15
ctctattgtt ggatcatatt cgtccacaaa atgattctga attagctgta tcgtcaaggc      60
actcttgcct acgccacaag ctccaactac acaagttta tattcagtca t              111
```